(12) United States Patent
Bethge

(10) Patent No.: US 10,513,536 B2
(45) Date of Patent: Dec. 24, 2019

(54) METHODS FOR THE PREPARATION OF A POLYALKOXYLATED NUCLEIC ACID MOLECULE

(71) Applicant: NOXXON Pharma AG, Berlin (DE)

(72) Inventor: Lucas Bethge, Potsdam (DE)

(73) Assignee: NOXXON Pharma AG, Berlin (DE)

( * ) Notice: Subject to any disclaimer, the term of this patent is extended or adjusted under 35 U.S.C. 154(b) by 313 days.

(21) Appl. No.: 15/116,050

(22) PCT Filed: Feb. 3, 2015

(86) PCT No.: PCT/EP2015/000207
§ 371 (c)(1),
(2) Date: Aug. 2, 2016

(87) PCT Pub. No.: WO2015/113776
PCT Pub. Date: Aug. 6, 2015

(65) Prior Publication Data
US 2017/0166604 A1    Jun. 15, 2017

(30) Foreign Application Priority Data

Feb. 3, 2014  (EP) .................................. 14000383
Nov. 18, 2014  (EP) .................................. 14003873

(51) Int. Cl.
*C07H 21/04* (2006.01)
*C07H 21/02* (2006.01)
*A61K 47/60* (2017.01)

(52) U.S. Cl.
CPC ............. *C07H 21/04* (2013.01); *A61K 47/60* (2017.08); *C07H 21/02* (2013.01)

(58) Field of Classification Search
CPC .............................. C07H 21/04; C07H 21/02
See application file for complete search history.

(56) References Cited

U.S. PATENT DOCUMENTS

| | | | |
|---|---|---|---|
| 8,207,298 B2* | 6/2012 | Hatala | C07H 21/00 210/690 |
| 8,841,431 B2 | 9/2014 | Sell et al. | |
| 2009/0286955 A1 | 11/2009 | Hatala | |
| 2015/0232852 A1 | 8/2015 | Purschke et al. | |

FOREIGN PATENT DOCUMENTS

WO    2012/025251    3/2012

OTHER PUBLICATIONS

Bondra, "Polyethylene . . . oligonucleotides," Appl Biochem Biotech Part A Enz Eng 54(1-3)3-17, 1995.
Bondra, "Polymer . . . oligonucleotides," J Bioactive Comp Poly 17(5)377-378, 2002.
Hoffman et al., "RNA . . . Conjugation," Curr Protocols NA Chem p. 4.46.1-4.46.30, John Wiley, NJ, 2011.

* cited by examiner

Primary Examiner — Lawrence E Crane
(74) Attorney, Agent, or Firm — MDIP LLC

(57) ABSTRACT

A method of obtaining a polyalkoxylated nucleic acid, which can be used to make a modified drug, from a liquid mixture of polyalkoxylated and non-polyalkoxylated nucleic acids is described. The method involves use of a solvent or a mixture of solvents that allow the polyalkoxylated nucleic acids to precipitate out of the solution.

17 Claims, 14 Drawing Sheets

Specification includes a Sequence Listing.

building blocks for 5'-amino-modifications building blocks for internal amino-modifications building blocks for 3'-amino-modifications

A)

B)

C)
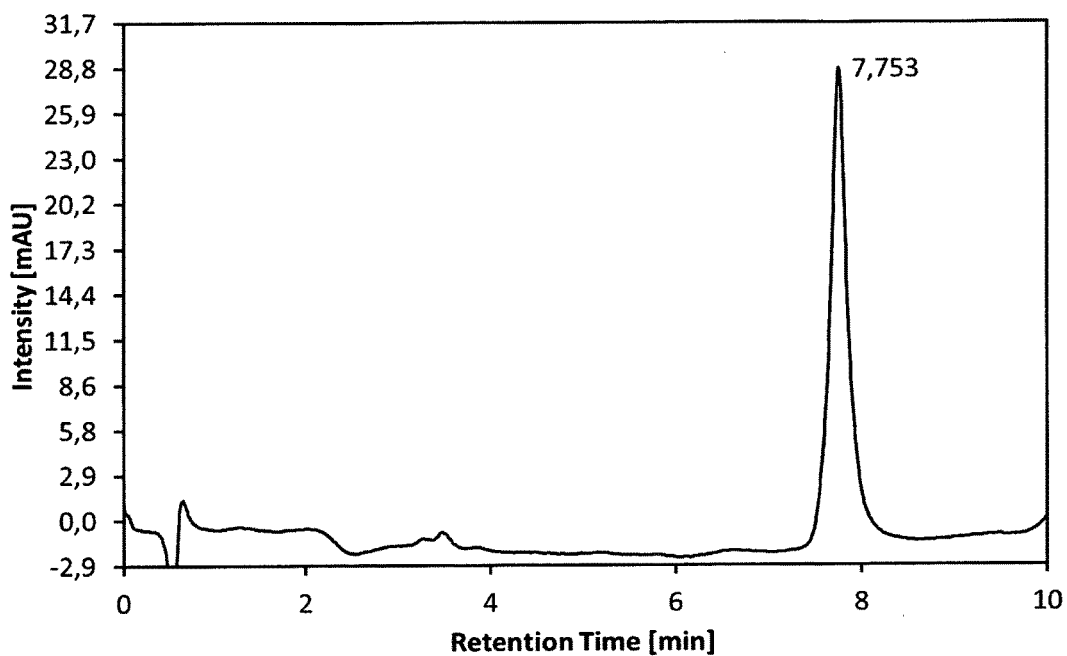
D)
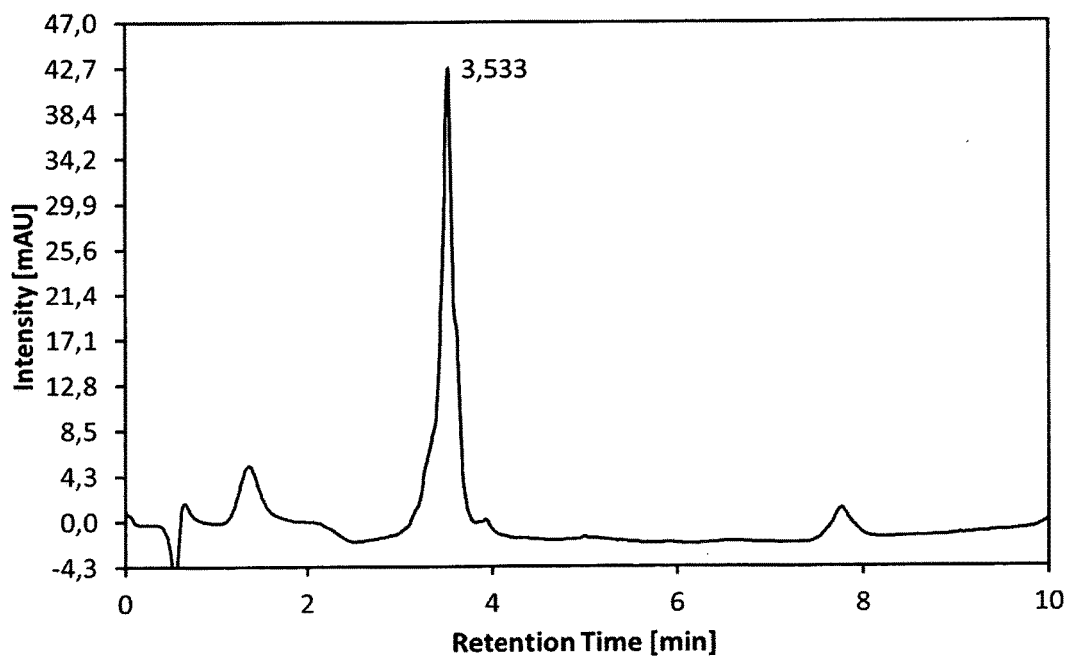
Continuation of Figure 3

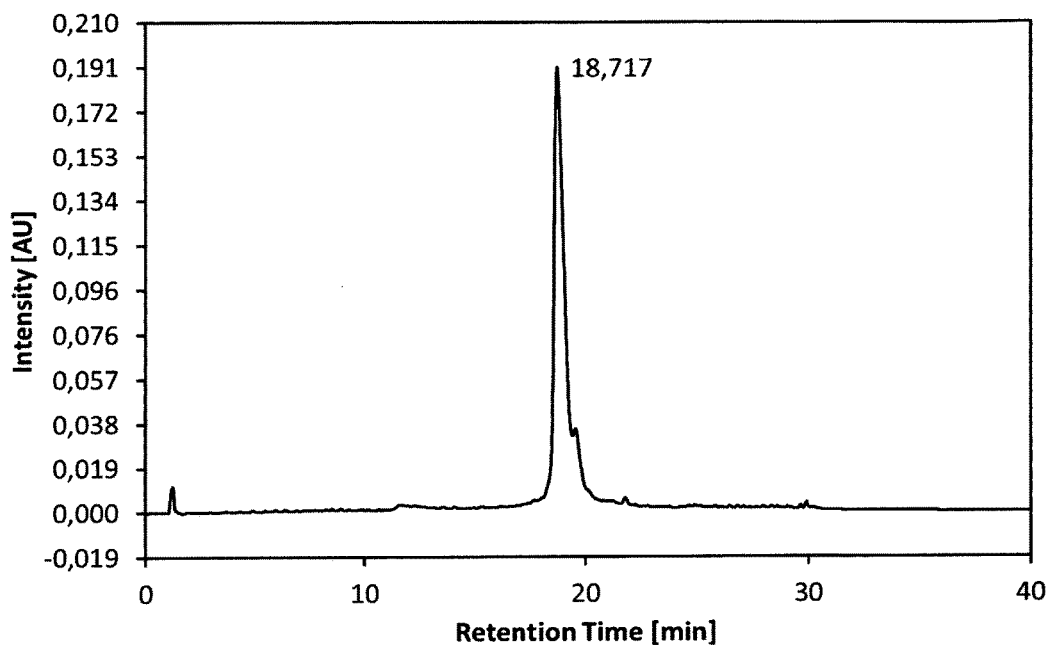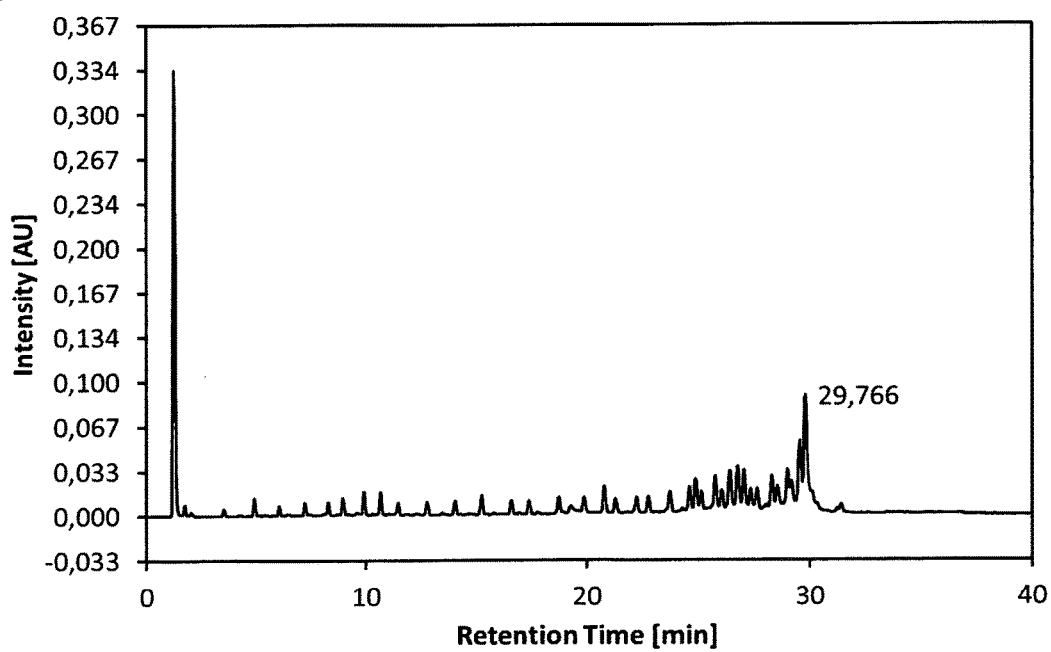
Continuation of Figure 3

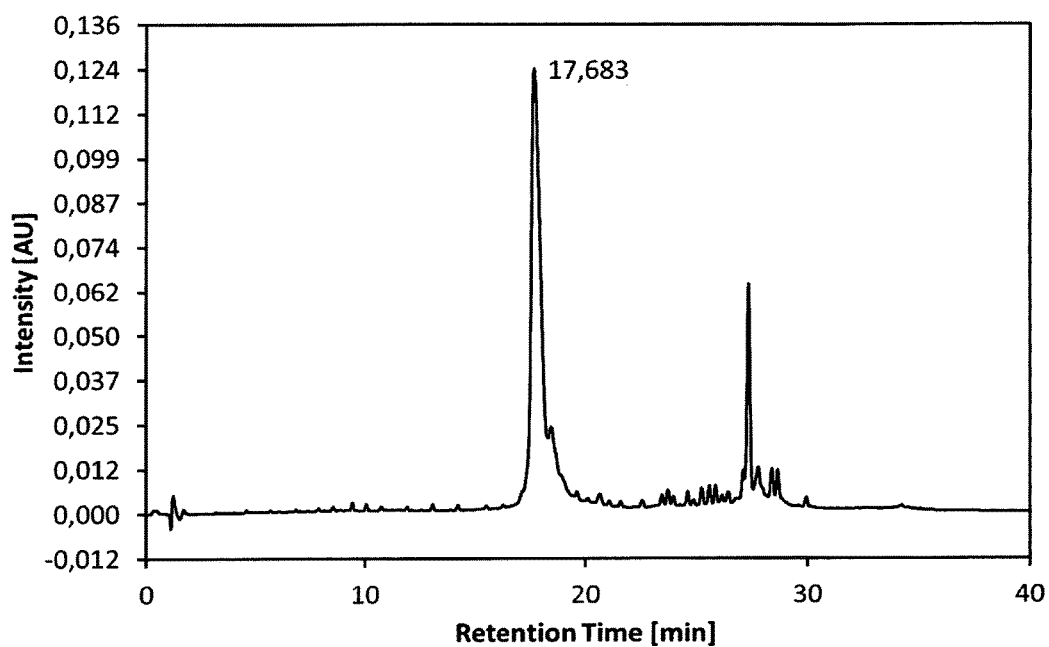
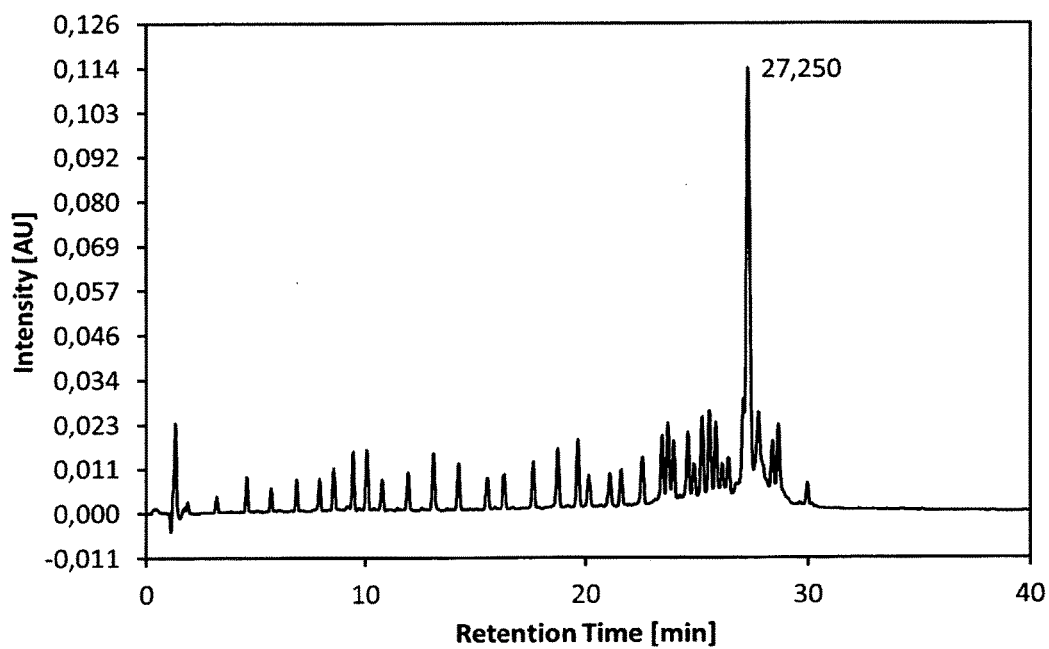
Continuation of Figure 4

A)

B)

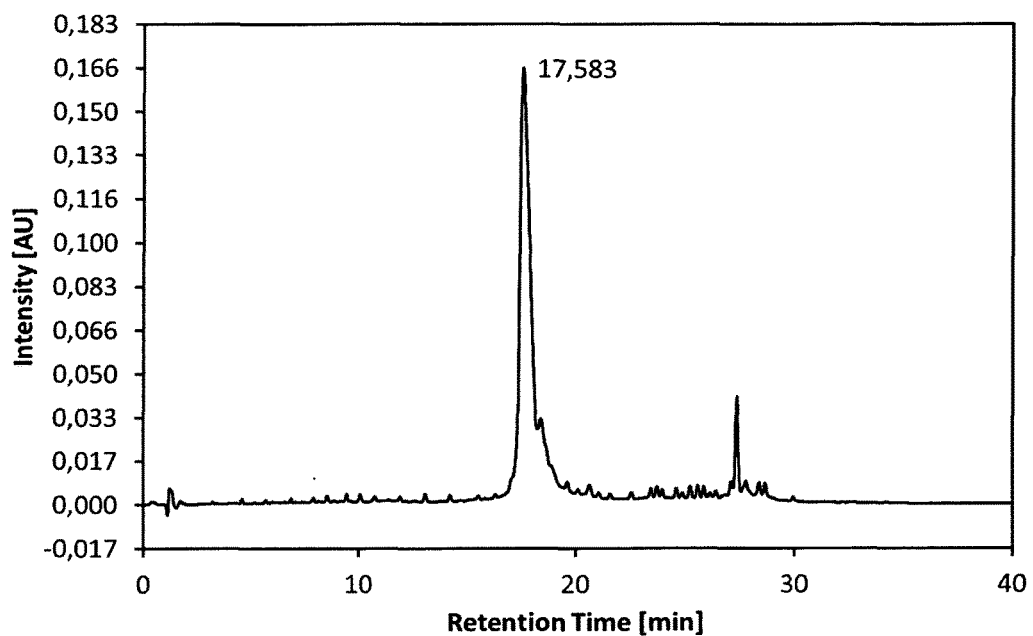
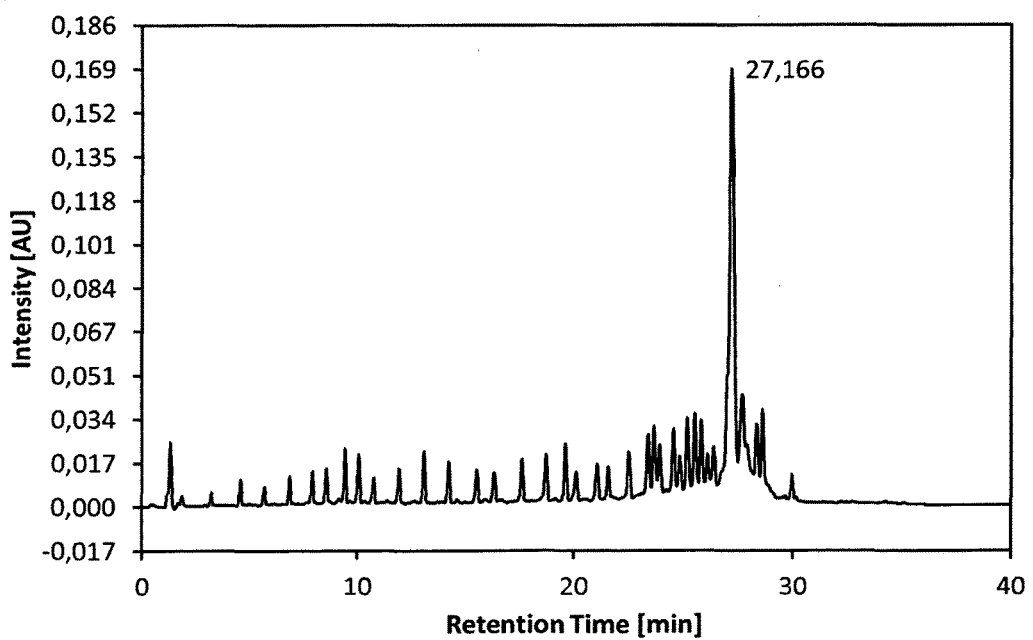
Continuation Figure 5

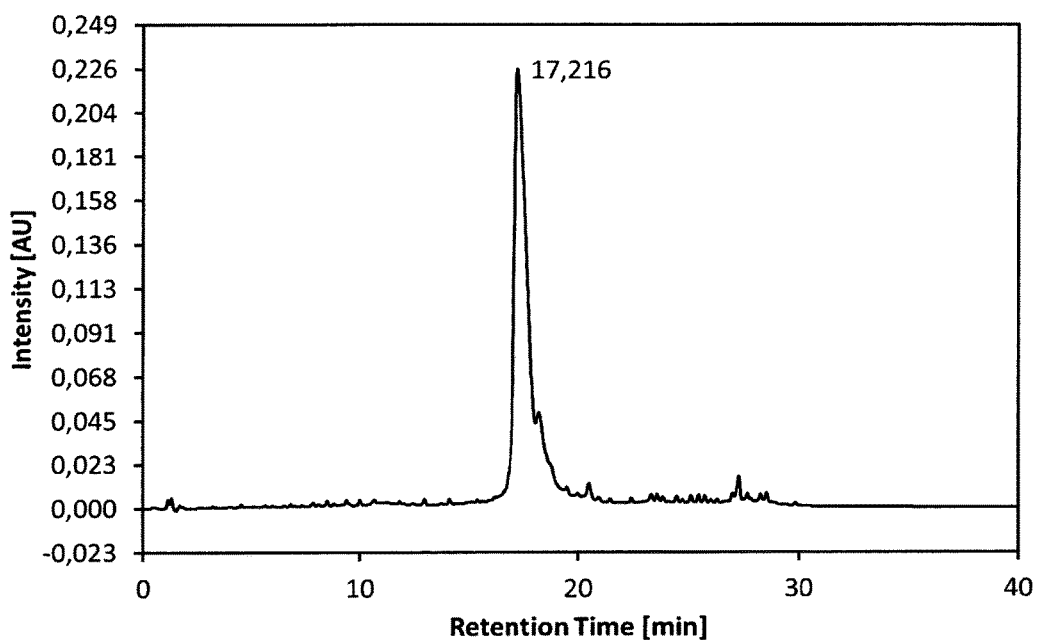
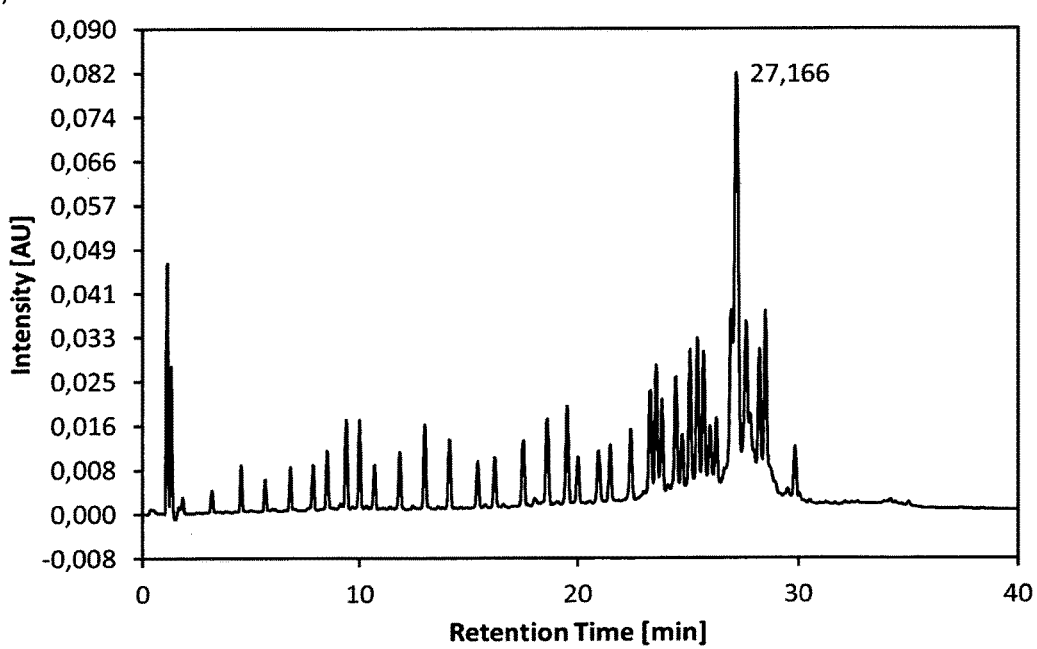
Continuation of Figure 6

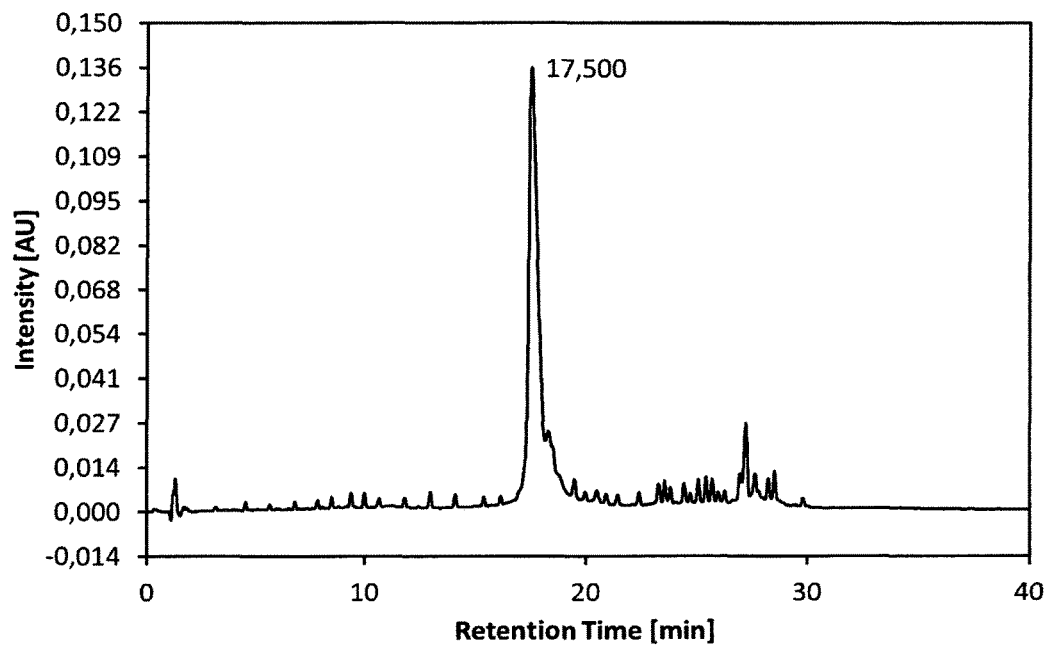
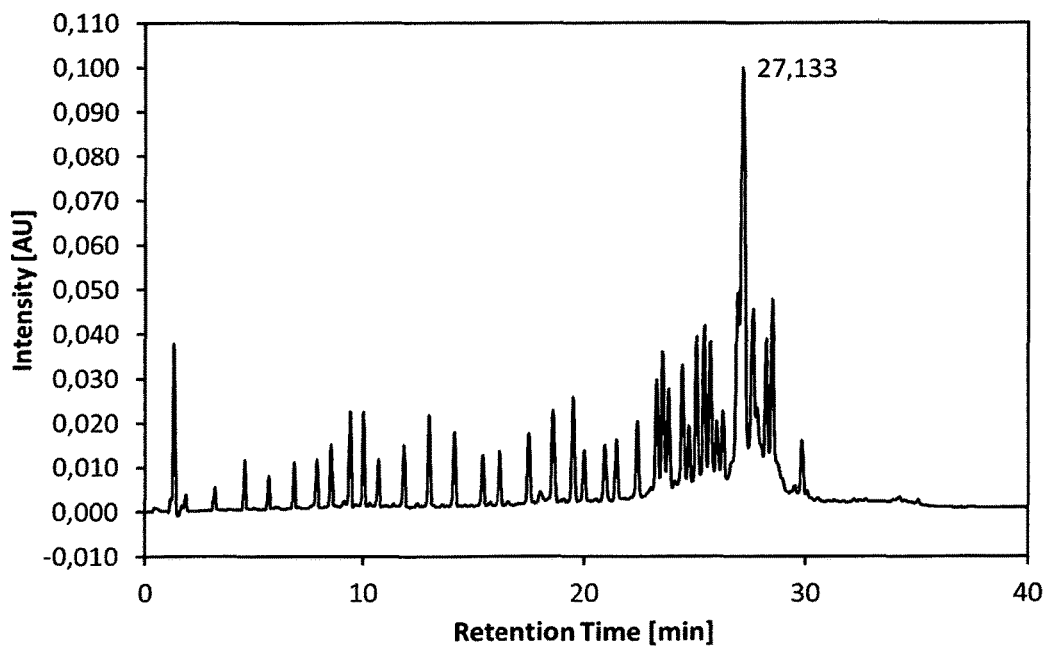
Continuation of Figure 7

Figure 8

| No | Sequence | Length | Typ | PEG load | Alternative Name |
|---|---|---|---|---|---|
| 1 | 5'-[40 kDa PEG]-amC6-rG-rC-rG-rU-rG-rC-rU-rG-rC-rA-rC-rG-rU-rC-rC-rU-rC-rA-rC-rC-rG-rU-rG-rC-rA-rA-rG-rU-rG-rA-rA-rG-rC-rC-rG-rU-rG-rC-rU-rC-rG-rC-rG-3' | 40nt | L-RNA | 40kDa | NOX-E36-40kDaYPEG |
| 2 | 5'-[20 kDa PEG]-amC6-rG-rC-rG-rU-rG-rC-rU-rG-rC-rA-rC-rG-rU-rC-rC-rU-rC-rA-rC-rC-rG-rU-rG-rC-rA-rA-rG-rU-rG-rA-rA-rG-rC-rC-rG-rU-rG-rC-rU-rC-rG-rC-rG-3' | 40nt | L-RNA | 20kDa | NOX-E36-20kDaPEG |
| 3 | 5'-[10 kDa PEG]-amC6-rG-rC-rG-rU-rG-rC-rU-rG-rC-rA-rC-rG-rU-rC-rC-rU-rC-rA-rC-rC-rG-rU-rG-rC-rA-rA-rG-rU-rG-rA-rA-rG-rC-rC-rG-rU-rG-rC-rU-rC-rG-rC-rG-3' | 40nt | L-RNA | 10kDa | NOX-E36-10kDaPEG |
| 4 | 5'-[40 kDa PEG]-amC3glycerol-rG-rC-rA-rC-rG-rU-rC-rC-rU-rC-rA-rC-rC-rG-rU-rG-rC-rA-rA-rG-rU-rG-rA-rA-rG-rC-rC-rG-rU-rG-rC-rU-rC-rG-rC-rG-rC-rG-3' | 40nt | L-RNA | 80kDa | NOX-E36-2x40kDaYPEG |
| 5 | 5'-[40 kDa PEG]-amC6-rG-rC-rG-rC-rG-rU-rG-rC-rU-rG-rC-rU-rA-rC-rG-rU-rC-rC-rU-rC-rA-rC-rC-rG-rU-rG-rC-rA-rA-rG-rU-rG-rA-rA-rG-rC-rC-rG-rU-rG-rA-rC-rG-rC-3' | 45nt | L-RNA | 40kDa | NOX-A12-40kDaYPEG |
| 6 | 5'-[40 kDa PEG]-amC6-rG-rC-rG-rU-rG-rC-rU-rG-rC-rU-rA-rC-rG-rU-rC-rC-rU-rC-rA-rC-rC-rG-rU-rG-rC-rA-rA-rG-rU-rG-rA-rA-rG-rC-rC-rG-rU-rG-rC-rG-rC-3' | 44nt | L-RNA | 40kDa | NOX-H94-40kDaYPEG |
| 7 | 5'-[40 kDa PEG]-amC6-rG-rC-rG-rU-rG-rU-rA-rG-rG-rC-rU-rU-rA-rG-rG-rC-rG-rA-rA-rG-rU-rC-rG-rG-rC-rG-rGrG-rC-3' | 19nt | L-RNA | 40kDa | NOX-A14-40kDaYPEG |
| 8 | 5'-[40kDa PEG]-amC6-dA-dC-dT-dC-dG-dA-dG-dG-dA-dA-dG-dG-dA-dA-dG-dG-dT-dG-dA-dA-dT-dG-dG-dT-dT-dG-dG-dA-dT-dT-dG-dC-dA-dT-dC-dC-dG-dA-dG-dT-3' | 46nt | L-DNA | 40kDa | NOX-G12-40kDaYPEG |
| 9 | 5'-[40 kDa PEG]-amC6-dG-dG-dT-dT-dG-dG-dT-dG-dT-dG-dG-dT-dT-dG-dG-3' | 15nt | D-DNA | 40kDa | Thrombin-binding DNA aptamer (TBA-40kDaYPEG) |

SEQUENCE LISTING

```
<160> NUMBER OF SEQ ID NOS: 9

<210> SEQ ID NO 1
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-ribonucleotide
<220> FEATURE:
<221> NAME/KEY: misc_feature
<222> LOCATION: (1)..(1)
<223> OTHER INFORMATION: 40 kDa PEG attached by C6 amino modifier

<400> SEQUENCE: 1
gcacgucccu caccggugca agugaagccg uggcucugcg                            40

<210> SEQ ID NO 2
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-ribonucleotide
<220> FEATURE:
<221> NAME/KEY: misc_feature
```

```
<222> LOCATION: (1)..(1)
<223> OTHER INFORMATION: 20 kDa PEG attached by C6 amino modifier

<400> SEQUENCE: 2
gcacgucccu caccggugca agugaagccg uggcucugcg                          40

<210> SEQ ID NO 3
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-ribonucleotide
<220> FEATURE:
<221> NAME/KEY: misc_feature
<222> LOCATION: (1)..(1)
<223> OTHER INFORMATION: 10 kDa PEG attached by C6 amino modifier

<400> SEQUENCE: 3
gcacgucccu caccggugca agugaagccg uggcucugcg                          40

<210> SEQ ID NO 4
<211> LENGTH: 40
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-ribonucleotide
<220> FEATURE:
<221> NAME/KEY: misc_feature
<222> LOCATION: (1)..(1)
<223> OTHER INFORMATION: 40 kDa PEG attached by C6 amino modifier

<400> SEQUENCE: 4
gcacgucccu caccggugca agugaagccg uggcucugcg                          40

<210> SEQ ID NO 5
<211> LENGTH: 45
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(45)
<223> OTHER INFORMATION: L-ribonucleotide
<220> FEATURE:
<221> NAME/KEY: misc_feature
<222> LOCATION: (1)..(1)
<223> OTHER INFORMATION: 40 kDa PEG attached by C6 amino modifier

<400> SEQUENCE: 5
gcguggugug aucuagaugu auuggcugau ccuagucagg uacgc                    45

<210> SEQ ID NO 6
<211> LENGTH: 44
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(44)
<223> OTHER INFORMATION: L-ribonucleotide
<220> FEATURE:
```

```
<221> NAME/KEY: misc_feature
<222> LOCATION: (1)..(1)
<223> OTHER INFORMATION: 40 kDa PEG attached by C6 amino modifier

<400> SEQUENCE: 6
gcgccguaug ggauuaagua aaugaggagu uggaggaagg gcgc                44

<210> SEQ ID NO 7
<211> LENGTH: 29
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: L-ribonucleotide
<220> FEATURE:
<221> NAME/KEY: misc_feature
<222> LOCATION: (1)..(1)
<223> OTHER INFORMATION: 40 kDa PEG attached by C6 amino modifier

<400> SEQUENCE: 7
gccgggguua gggcuagaag ucggccggc                                29

<210> SEQ ID NO 8
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(46)
<223> OTHER INFORMATION: L-deoxynucleotide
<220> FEATURE:
<221> NAME/KEY: misc_feature
<222> LOCATION: (1)..(1)
<223> OTHER INFORMATION: 40 kDa PEG attached by C6 amino modifier

<400> SEQUENCE: 8
actcgagagg aaaggttggt aaaggttcgg ttggattcac tcgagt             46

<210> SEQ ID NO 9
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: D-deoxynucleotide
<220> FEATURE:
<221> NAME/KEY: misc_feature
<222> LOCATION: (1)..(1)
<223> OTHER INFORMATION: 40 kDa PEG attached by C6 amino modifier

<400> SEQUENCE: 9
ggttggtgtg gttgg                                               15
```

METHODS FOR THE PREPARATION OF A POLYALKOXYLATED NUCLEIC ACID MOLECULE

CROSS REFERENCE TO RELATED APPLICATION

The instant application is a 371 national stage filing of PCT Ser. No. EP 2015/00207 filed 3 Mar. 2015.

BACKGROUND OF THE INVENTION

The present invention is related to methods for the preparation of a polyalkoxylated nucleic acid molecule and a polyalkoxylated nucleic acid obtainable by such methods.

Attachment of polyalkoxylates such as polyalkylene glycols to drugs, such as small molecules, nucleic acid molecules, peptides, proteins and nanoparticles is widely used to increase the bioavailability, stability, safety, and efficacy of such drugs for therapeutic applications. Within the field of nucleic acid based drugs, aptamers and spiegelmers which are also referred to as mirror-image aptamers, are typically polyalkoxylated. Polyethylene glycol (abbr. PEG) is a typically used polyalkoxylate that has been approved by the Food and Drug Administration as part of drugs administered intravenously, orally and dermally.

In general, a polyalkoxylated nucleic acid molecule is prepared by a process that first assembles the nucleic acid molecule containing a reactive group on a solid phase. Such process is, for example, described in Hoffmann et al. (Hoffmann et. al, Current Protocols in Nucleic Acid Chemistry 2011, 4:4.46.1-4.46.30) and illustrated in FIG. 1A herein. After cleavage from solid phase the crude synthesis product can be purified by various processes such as Reversed Phase High Performance Liquid Chromatography (abbr. RP-HPLC), Ion Exchange Chromatography High Performance Liquid Chromatography (abbr. IEX-HPLC) and ultrafiltration or any combination thereof. Typically, such process consists of a combination of RP-HPLC or IEX-HPLC and ultrafiltration to yield a nucleic acid molecule comprising the desired nucleotide sequence and a reactive group for subsequent attachment of the polyalkoxylate. This reactive group can subsequently be reacted with a polyalkoxylate comprising a suitable reactive group capable of forming a covalent bond with the nucleic acid molecule and the reactive group provided by such nucleic acid molecule. After the conjugation reaction the thus obtained crude product is again purified by a process such as RP-HPLC, IEX-HPLC or ultrafiltration or any combination thereof.

The yield of a polyalkoxylation reaction depends on the purity of the nucleic acid molecule to be polyalkoxylated and on the reaction conditions itself. Because of that, typically the nucleic acid molecule to be polyalkoxylated is purified by HPLC and/or ultrafiltration before polyalkoxylation reaction. Standard conditions for polyalkoxylation reaction are as follows: The amino modified nucleic acid molecule is prepared in an aqueous solution and a base is added. Typically, the base is 100 mM sodium borate or sodium bicarbonate. Finally the polyalkoxylate-N-hydroxy succinimide ester (abbr. polyalkoxylate-NHS) is added dissolved in a water miscible organic solvent such as DMF or DMSO. The yield for a polyalkoxylated nucleic acid molecule is between 75 and 95% and largely depends on the equivalents of polyalkoxylate-NHS used. The yield suffers from the competing hydrolytic cleavage of the polyalkoxylate-NHS. Therefore, usually several equivalents of polyalkoxylate-NHS are added in several portions over time and the turnover is monitored by analytical methods.

Typically, therapeutic aptamers and spiegelmers consist of about 30 to 50 nucleotides (Keefe et. al., Nature Reviews, 2010, 9, 537; James, Encyclopedia of Analytical Chemistry, 2000, 4848). Although average stepwise coupling efficacy is close to 99%, a great number of nucleic acid molecules of truncated failure sequences of various lengths is accumulated during solid phase synthesis. For the separation of these truncated failure sequences from the desired full length nucleic acid species the properties of the finally coupled nucleotide, of a linker or modifier used in the attachment of the polyalkoxylate to the nucleic acid molecule and the nucleotide, respectively, or of the subsequently generated conjugate to the modifier is exploited as nucleic acid species having capped truncated sequences do not possess this building block. For example, in a 3'- to 5'-directed synthesis the 5'MMT- or 5'DMT-group of a C6-amino- or a C6-disulfide modifier can be used to achieve stronger interaction with IEX-HPLC or RP-HPLC-resins leading to later elution of full length species of the nucleic acid in comparisons to species having truncated failure species lacking the modification. Though the similar affinity effects can be used to separate unreacted truncated failure sequences of the polyalkoxylation reaction from the desired polyalkoxylated full length nucleic acid molecule, it is advantageous to remove the failure sequences prior to the final HPLC-purification as the resolution and efficiency of the chromatographic purification is influenced by the impurities. Purification by HPLC of polyalkoxylated nucleic acids such as, for example, aptamers and spiegelmers, however, is time consuming, laborious and involves expensive resins.

In light of the above, the production of polyalkoxylated nucleic acids involves numerous steps of synthesis and purification which are time and money consuming. Accordingly, there is a strong need to optimize the production of polyalkoxylated nucleic acids.

BRIEF SUMMARY OF THE INVENTION

These and other problems underlying the present invention are solved by the subject matter of the instant invention and of the attached independent claims in particular. Preferred embodiments may be taken from the attached dependent claims.

More specifically, the problem underlying the present invention is solved in a first aspect by a method for the preparation of a polyalkoxylated nucleic acid molecule, wherein the method comprises separating the polyalkoxylated nucleic acid molecule from a mixture of nucleic acid molecules, wherein the mixture of nucleic acid molecules comprises the polyalkoxylated nucleic acid molecule and a non-polyalkoxylated nucleic acid molecule, and wherein the polyalkoxylated nucleic acid molecule is separated from the non-polyalkoxylated nucleic acid molecule by precipitating the polyalkoxylated nucleic acid molecule from the mixture.

In an embodiment of the first aspect, the polyalkoxylated nucleic acid molecule comprises a nucleic acid moiety and at least one polyalkoxylate moiety, and wherein the non-polyalkoxylated nucleic acid molecule comprises one nucleic acid moiety and is lacking a polyalkoxylate moiety.

In an embodiment of the first aspect, the polyalkoxylated nucleic acid molecule is a plurality of different species of a polyalkoxylated nucleic acid molecule.

In an embodiment of the first aspect, the non-polyalkoxylated nucleic acid molecule is a plurality of different species of a non-polyalkoxylated nucleic acid molecule In an embodiment of the first aspect, the different species of a polyalkoxylated nucleic acid molecule differ in terms of their nucleic acid moieties, wherein preferably the different species of a polyalkoxylated nucleic acid molecule differ in terms of the nucleotide sequence of the nucleic acid moieties.

In an embodiment of the first aspect, the different species of a non-polyalkoxylated nucleic acid molecule differ in terms of their nucleic acid moieties, wherein preferably the different species of a non-polyalkoxylated nucleic acid molecule differ in terms of the nucleotide sequence of the nucleic acid moieties.

In an embodiment of the first aspect, the molecular weight of the nucleic acid moiety of the non-polyalkoxylated nucleic acid molecule is lower than the molecular weight of the nucleic acid moiety of the polyalkoxylated nucleic acid molecule.

In an embodiment of the first aspect, the nucleic acid moiety of the non-polyalkoxylated nucleic acid molecule comprises less nucleotides than the nucleic acid moiety of the polyalkoxylated nucleic acid molecule.

In an embodiment of the first aspect, the mixture of nucleic acid molecules comprising the polyalkoxylated nucleic acid molecule and a non-polyalkoxylated nucleic acid molecule is a solution, wherein the solution consists of a solvent or a mixture of solvents comprising more than one solvent.

In an embodiment of the first aspect, the solvent comprises water.

In an embodiment of the first aspect, the solvent comprises one or more water miscible organic solvent(s).

In an embodiment of the first aspect, the water miscible organic solvent(s) is/are selected from the group comprising methanol, ethanol, n-propanol, isopropanol, n-butanol, sec-butanol, tert-butanol, dimethyl sulfoxid, diethyl sulfoxide, methyl ethyl sulfoxide, formamide, methyl formamide, dimethyl formamide, ethyl formamide, ethyl methyl formamide, diethyl formamide, 2-pyrrolidone, N-methyl pyrrolidone, N-ethylpyrrolidone, acetonitrile, acetone, ethyl methyl ketone, methyl propyl ketone, diethyl ketone, methyl ispropyl ketone, methyl formate, ethyl formate, propyl formate, isopropyl formate, methyl acetate, ethyl acetate, methyl propanoate, tetrahydrofuran, dioxan.

In an embodiment of the first aspect, the water miscible organic solvent(s) provides for a volume fraction of 5% to 95% of the solution.

In an embodiment of the first aspect, the step of precipitating the polyalkoxylated nucleic acid molecule from the mixture is carried at a temperature of −50° C. to 30° C., preferably at a temperature of −25° C. to 25° C., more preferably at a temperature of −20° C. to 4° C., most preferably at a temperature of −20° C. or at a temperature of 4° C.

In an embodiment of the first aspect, the step of precipitating is carried at a temperature of −20° C. to 4° C. for 30 min to 16 hours before the precipitated polyalkoxylated nucleic acid molecule is separated from a supernatant formed by the mixture of nucleic acid molecules comprising the polyalkoxylated nucleic acid molecule and a non-polyalkoxylated nucleic acid molecule upon precipitation of the polyalkoxylated nucleic acid molecule.

In an embodiment of the first aspect, the step of precipitating is carried out at a temperature of −20° C. for 30 min to 16 hrs before the precipitated polyalkoxylated nucleic acid molecule is separated from a supernatant formed by the mixture of nucleic acid molecules comprising the polyalkoxylated nucleic acid molecule and a non-polyalkoxylated nucleic acid molecule upon precipitation of the polyalkoxylated nucleic acid molecule.

In an embodiment of the first aspect, the step of precipitating is carried out at a temperature of 4° C. for 16 hrs before the precipitated polyalkoxylated nucleic acid molecule is separated from a supernatant formed by the mixture of nucleic acid molecules comprising the polyalkoxylated nucleic acid molecule and a non-polyalkoxylated nucleic acid molecule upon precipitation of the polyalkoxylated nucleic acid molecule.

In an embodiment of the first aspect, the step of precipitating the polyalkoxylated nucleic acid molecule from the mixture of nucleic acid molecules comprising the polyalkoxylated nucleic acid molecule and a non-polyalkoxylated nucleic acid molecule is carried at a pH range of 4 to 11, preferably at a pH range of 6 to 10 and more preferably at a pH range of 7 to 9.5.

In an embodiment of the first aspect, the step of precipitating the polyalkoxylated nucleic acid molecule from the mixture of nucleic acid molecules comprising the polyalkoxylated nucleic acid molecule and a non-polyalkoxylated nucleic acid molecule is carried out until 75% to 100% of the polyalkoxylated nucleic acid molecule is precipitated, preferably until 90% to 100% of polyalkoxylated nucleic acid molecule is precipitated.

In an embodiment of the first aspect, the precipitated polyalkoxylated nucleic acid molecule is separated from the non-polyalkoxylated nucleic acid molecule by a separation method for the separation of a liquid from a solid.

In an embodiment of the first aspect, the separation method for the separation of a liquid from a solid is selected from the group comprising filtration, centrifugation, and decantation.

In an embodiment of the first aspect, the polyalkoxylate moiety is a straight or branched polyalkoxylate moiety.

In an embodiment of the first aspect, the polyalkoxylate moiety is selected from the group comprising polyethylene glycol, polypropylene glycol, poly butylene glycol, polyglycerol.

In an embodiment of the first aspect, the polyalkoxylate moiety is polyethylene glycol.

In an embodiment of the first aspect, the polyalkoxylate moiety has a molecular weight of 5,000 Da to 100,000 Da, preferably of 20,000 Da to 80,000 Da, more preferably 40,000 Da.

In an embodiment of the first aspect, the nucleic acid moiety of the polyalkoxylated nucleic acid molecule and/or of the non-polyalkoxylated nucleic acid molecule has each a molecular weight of 300 Da to 50,000 Da, preferably 3,000 Da to 35,000 Da and more preferably 3,000 Da to 16,000 Da.

In an embodiment of the first aspect, the nucleic acid moiety of the polyalkoxylated nucleic acid molecule and/or of the non-polyalkoxylated nucleic acid molecule is an aptamer or a spiegelmer.

More specifically, the problem underlying the present invention is solved in a second aspect by a method for the preparation of a polyalkoxylated nucleic acid molecule comprising a nucleic acid moiety and a polyalkoxylate moiety, wherein the method comprises reacting a nucleic acid molecule with a polyalkoxylate thereby forming the polyalkoxylated nucleic acid molecule, wherein the reaction is carried out in the presence of a quaternary ammonium compound, and wherein the nucleic acid molecule forms the nucleic acid moiety of the polyalkoxylated nucleic acid moiety and the polyalkoxylate forms the polyalkoxylate moiety of the polyalkoxylated nucleic acid molecule.

In an embodiment of the second aspect, the quaternary ammonium compound is selected from the group comprising tetraalkyl ammonium chloride, tetraalkyl ammonium bromide, tetraalkyl ammonium tertrafluoro borate, tetraalkyl hexafluoro phosphate, tetraalkyl hydrogen sulphate, tetraalkyl hydrogen phosphate, wherein alkyl is an alkyl chain consisting of 1 to 18 C-atoms, wherein preferably the quaternary ammonium compound is tetrabutyl ammonium bromide.

In an embodiment of the second aspect, the quaternary ammonium compound is dissolved in water or a water miscible organic solvent or a combination thereof.

In an embodiment of the second aspect, the water miscible organic solvent is selected from the group comprising dimethyl sulfoxide, diethyl sulfoxide, methyl ethyl sulfoxide, methyl formamide, dimethyl formamide, ethyl formamide, ethyl methyl formamide, diethyl formamide, 2-pyrrolidone, N-methyl pyrrolidone, N-ethylpyrrolidone, acetonitrile, acetone, ethyl methyl ketone, methyl propyl ketone, diethyl ketone, methyl ispropyl ketone, methyl formate, ethyl formate, propyl formate, isopropyl formate, methyl acetate, ethyl acetate, methyl propanoate, tetrahydrofuran, dioxan.

In an embodiment of the second aspect, the quaternary ammonium compound is dissolved in dimethyl formamide, wherein preferably the quaternary ammonium compound is tetrabutyl ammonium bromide.

In an embodiment of the second aspect, the reaction is carried out in the presence of 1 to 20 mole equivalents of the quaternary ammonium compound per nucleotide of the nucleic acid molecule, preferably 2 to 10 mole equivalents per nucleotide of the nucleic acid molecule.

In an embodiment of the second aspect, the reaction is carried out at a temperature of 10° C. to 50° C., preferably at a temperature of 20° C. to 40° C.

In an embodiment of the second aspect, the reaction is carried out at a pH range of 4 to 11, preferably at a pH range of 6 to 10.

In an embodiment of the second aspect, the polyalkoxylate moiety of the polyalkoxylated nucleic acid molecule consists of one polyalkoxylate moiety or more than one polyalkoxylate moieties.

In an embodiment of the second aspect, the polyalkoxylate moiety is a straight or branched polyalkoxylate moiety.

In an embodiment of the second aspect, the polyalkoxylate moiety is selected from the group comprising polyethylene glycol, polypropylene glycol, polybutylene glycol and polyglycerol.

In an embodiment of the second aspect, the polyalkoxylate moiety is polyethylene glycol.

In an embodiment of the second aspect, the nucleic acid molecule comprises at least one reactive group, preferably more than one reactive groups, wherein the more than one reactive groups are different reactive groups, and the polyalkoxylate comprises a reactive group capable of reacting with the at least one reactive group of the nucleic acid molecule forming the polyalkoxylated nucleic acid molecule.

In an embodiment of the second aspect, the reactive group of the nucleic acid molecule is selected from the group comprising an amine, a thiol, an azide, an alkyne, a carboxylate, a carboxylic acid ester, an aldehyde, an iodoalkyl and a maleimide, wherein preferably the reactive group of the nucleic acid molecule is an amine.

In an embodiment of the second aspect, the reactive group of the polyalkoxylate is selected from the group comprising an amine, a thiol, an azide, an alkyne, a carboxylate, a carboxylic acid ester, an aldehyde, an iodoalkyl and a maleimide, wherein preferably the reactive group of the polyalkoxylate is a carboxylic acid ester, wherein more preferably the reactive group of the polyalkoxylate is an N-hydroxy succinimide ester.

In an embodiment of the second aspect, the reactive group of the nucleic acid molecule is an amine and the reactive group of the polyalkoxylate is an N-hydroxy succinimide ester.

In an embodiment of the second aspect, the polyalkoxylate moiety and/or the polyalkoxylate has a molecular weight of 5,000 Da to 100,000 Da, preferably of 20,000 Da to 80,000 Da, more preferably 40,000 Da.

In an embodiment of the second aspect, the nucleic acid molecule moiety and/or the nucleic acid moiety has a molecular weight of 300 Da to 50,000 Da, preferably 3,000 Da to 35,000 Da and more preferably 3,000 Da to 16,000 Da.

In an embodiment of the second aspect, the nucleic acid molecule is an aptamer or a spiegelmer.

More specifically, the problem underlying the present invention is solved in a third aspect by a method for the preparation of a polyalkoxylated nucleic acid molecule comprising
a) a method for the preparation of a polyalkoxylated nucleic acid molecule, wherein the method comprises the reaction of a nucleic acid molecule with a polyalkoxylate thereby forming the polyalkoxylated nucleic acid molecule, and
b) a method according to the first aspect.

In an embodiment of the third aspect, the method for the preparation of a polyalkoxylated nucleic acid molecule comprises a method according to the second aspect.

More specifically, the problem underlying the present invention is solved in a fourth aspect by a method for the preparation of a polyalkoxylated nucleic acid molecule comprising
a) synthesizing a non-polyalkoxylated nucleic acid molecule on a solid support,
b) cleaving the non-polyalkoxylated nucleic acid molecule from the solid support and deprotecting the non-polyalkoxylated nucleic acid molecule,
c) desalting the non-polyalkoxylated nucleic acid molecule using ultrafiltration,
d) polyalkoxylation of the non-polyalkoxylated nucleic acid molecule to produce a polyalkoxylated nucleic acid molecule,
e) separating of the polyalkoxylated nucleic acid molecule, from non-polyalkoxylated nucleic acid molecules, by precipitation of the polyalkoxylated nucleic acid molecule,
f) purifying the polyalkoxylated nucleic acid molecule by HPLC,
g) desalting the polyalkoxylated nucleic acid molecule using ultrafiltration.

In an embodiment of the fourth aspect, the method further comprises step h) freeze drying the final product.

In an embodiment of the fourth aspect, step d) comprises a method according to the second aspect.

In an embodiment of the fourth aspect, step e) comprises a method according to the first aspect.

More specifically, the problem underlying the present invention is solved in a fifth aspect by a polyalkoxylated nucleic acid molecule, obtainable by a method according to the second aspect.

More specifically, the problem underlying the present invention is solved in a sixth aspect by a polyalkoxylated nucleic acid molecule, obtainable by a method according to the first aspect.

More specifically, the problem underlying the present invention is solved in a seventh aspect by a polyalkoxylated nucleic acid molecule, obtainable by a method according to the third aspect.

More specifically, the problem underlying the present invention is solved in an eighth aspect by a polyalkoxylated nucleic acid molecule, obtainable by a method according to the fourth aspect.

The present invention also provides a method for removing unreacted failure sequences from polyalkoxylated nucleic acids.

The present invention also provides a method for the preparation of polyalkoxylated nucleic acids from a nucleic acid starting material that has not been purified by a chromatographic process prior to polyalkoxylation.

DETAILED DESCRIPTION OF THE INVENTION

The inventors have surprisingly found that polyalkoxylated nucleic acid molecules can be separated from non-polyalkoxylated nucleic acid molecules by Precipitation. By means of such process, among others, the first chromatographic purification of the crude nucleic acid can be omitted and the efficiency of the second chromatographic purification of the nucleic acid conjugated to the polyalkoxylate can be improved Additionally, the present inventors have found a process for the preparation of a polyalkoxylated nucleic acid molecule which comprises reacting a nucleic acid molecule with a polyalkoxylate thereby forming a polyalkoxylated nucleic acid molecule, wherein the nucleic acid has not been purified by a chromatographic process prior to polyalkoxylation and the polyalkoxylated nucleic acid molecule is separated from the non-polyalkoxylated nucleic acid molecule by Precipitation, wherein the non-polyalkoxylated nucleic acid molecule is an undesired impurity of the nucleic acid synthesis such as truncated sequences. FIG. 1B shows a schematic drawing of the process according to the present invention.

The inventors have thus surprisingly found a protocol for polyalkoxylation of a nucleic acid molecule that allows a more efficient production of polyalkoxylated nucleic acids as known from state of the art.

Finally, the inventors have found that polyalkoxylated nucleic acids can be produced by the polyalkoxylation method of the present invention in the practicing of which the polyalkoxylated nucleic acid molecule is separated from a non-polyalkoxylated nucleic acid molecule by Precipitation.

The following is applicable to each and any aspect of the present invention and more specifically to each method for the preparation of a polyalkoxylated nucleic acid molecule according to the present invention and any polyalkoxylated nucleic acid molecule obtainable by such methods.

It is within the present invention that the mixture of nucleic acid molecules comprising the polyalkoxalated nucleic acid molecule and a non-polyalkoxylated nucleic acid molecule is a solution or is contained in a solution, wherein the solution comprises the polyalkoxylated nucleic acid molecule and a non-polyalkoxylated nucleic acid molecule. In accordance therewith it is within the method of the invention in its various embodiments that upon precipitating the polyalkoxylated nucleic acid molecule from the mixture of nucleic acid molecules comprising the polyalkoxalated nucleic acid molecule and a non-polyalkoxylated nucleic acid molecule, the polyalkoxylated nucleic acid molecule is present as a precipitate, whereas the non-polyalkoxylated nucleic acid molecule remains dissolved within the solution.

As preferably used herein, a polyalkoxylated nucleic acid molecule is a nucleic acid molecule which comprises at least a nucleic acid moiety and at least one polyalkoxylate moiety. The nucleic acid moiety comprises a nucleotide sequence. The polyalkoxylated nucleic acid molecule may comprise one or several polyalkoxylate moieties. In a preferred embodiment the polyalkoxylated nucleic acid molecule comprises a linker; preferably such linker links a polyalkoxylate moiety to the nucleic acid moiety. In an embodiment of the present invention where the polyalkoxylated nucleic acid molecule comprises two or more polyalkoxylate moieties each of the two or more polyalkoxylate moieties is attached to the nucleic acid moiety by means of a linker; such linkers can be the same or different for the individual polyalkoxylate moieties.

It is to be acknowledged that the linker is also referred to as modifier herein.

It is within the present invention that the polyalkoxylated nucleic acid molecule comprises one, two, three, four, five, six, seven, eight, nine, ten or more polyalkoxylate moieties. It is within the present invention that in case the polyalkoxylated nucleic acid molecule comprises two or more polyalkoxylate moieties the two or more polyalkoxylate moieties are attached at the same position or at different positions of the nucleic acid sequence moiety of the polyalkoxylated nucleic acid molecule.

In a preferred embodiment, the polyalkoxylated nucleic acid molecule comprises one polyalkoxylate moiety.

In an alternative preferred embodiment the polyalkoxylated nucleic acid molecule comprises two polyalkoxylate moieties. In an embodiment of the polyalkoxylated nucleic acid molecule comprising two polyalkoxylate moieties the two polyalkoxylate moieties are attached at the same position of the nucleic acid moiety. Preferably, such two moieties are attached to the 5'-terminal nucleotide of the nucleic acid moiety. In a first alternative, such two moieties are attached to the 3'-terminal nucleotide of the nucleic acid moiety. In a second alternative, such two moieties are attached to a nucleotide of the nucleic acid moiety within the nucleotide sequence of the nucleic acid moiety, whereby such nucleotide is different from the 5'-terminal nucleotide of the nucleic acid moiety and the 3'-terminal nucleotide of the nucleic acid moiety. In an alternative embodiment of the polyalkoxylated nucleic acid molecule comprising two polyalkoxylate moieties the two polyalkoxylate moieties are attached at different position of the nucleic acid moiety. In accordance therewith, a first polyalkoxylate moiety is attached to the 5'-terminal nucleotide of the nucleic acid moiety and a second polyalkoxylate moiety is attached to the 3'-terminal nucleotide of the nucleic acid moiety; or a first polyalkoxylate moiety is attached to the 5'-terminal nucleotide of the nucleic acid moiety and a second polyalkoxylate moiety is attached to a nucleotide of the nucleic acid moiety within the nucleotide sequence of the nucleic acid moiety, whereby such nucleotide is different from the 5'-terminal nucleotide of the nucleic acid moiety and the 3'-terminal nucleotide of the nucleic acid moiety; or a first polyalkoxylate moiety is attached to the 3'-terminal nucleotide of the nucleic acid moiety and a second polyalkoxylate moiety is attached to a nucleotide of the nucleic acid moiety within the nucleotide sequence of the nucleic acid moiety, whereby such nucleotide is different from the 5'-terminal nucleotide of the nucleic acid moiety and the 3'-terminal nucleotide of the nucleic acid moiety; or a first polyalkoxylate moiety is attached to a nucleotide of the nucleic acid moiety within the nucleotide sequence of the nucleic acid moiety, whereby such nucleotide is different from the 5'-terminal nucleotide of the nucleic acid moiety and the 3'-terminal nucleotide of the nucleic acid moiety, and wherein a second polyalkoxylate moiety is attached to a nucleotide of the nucleic acid sequence moiety within the nucleotide sequence of the nucleic acid moiety, whereby such nucleotide is different from the 5'-terminal nucleotide of the nucleic acid moiety, the 3'-terminal nucleotide of the nucleic acid moiety and the nucleotide to which the first polyalkoxylate moiety is attached.

As preferably used herein a non-polyalkoxylated nucleic acid molecule is a nucleic acid molecule which comprises a nucleic acid moiety but is lacking a polyalkoxylate moiety or is lacking any polyalkoxylate moieties, each as preferably defined herein. It is, however, within the present invention that the non-polyalkoxylated nucleic acid molecule comprises a linker which is used for linking a polyalkoxylate moiety to a nucleic acid moiety as defined herein. It is also within the present invention that the non-polyalkoxylated nucleic acid molecule is lacking said linker. Finally, it is also within the present invention that the non-polyalkoxylated nucleic acid molecule is a mixture of a non-polyalkoxylated nucleic acid molecule comprising the linker and a non-polyalkoxylated nucleic acid molecule lacking said linker.

In an embodiment of the various aspects of the present invention the term "a polyalkoxylated nucleic acid molecule" refers to a plurality of species of a polyalkoxylated nucleic acid molecule. Preferably, the individual species of such plurality differ from each other as to the nucleotide sequence of the nucleic acid moiety. Such difference in nucleotide sequence may, for example, result from the synthesis of the nucleic acid moiety. It is, however, also within the present invention that the individual species of such plurality have the same nucleotide sequence. It is, alternatively or additionally, also within the present invention that the individual species of such plurality differ from each other as to the polyalkoxylate moiety and moieties, respectively.

In an embodiment of the various aspects of the present invention the term "a non-polyalkoxylated nucleic acid molecule" refers to a plurality of species of a non-polyalkoxylated nucleic acid molecule. Preferably, the individual species of such plurality differ from each other as to the nucleotide sequence of the nucleic acid moiety. Such difference in nucleotide sequence may, for example, result from the synthesis of the nucleic acid moiety. It is, however, also within the present invention that the individual species of such plurality have the same nucleotide sequence.

It is also within the present invention that when it is referred to a polyalkoxylated nucleic acid molecule which is present or contained in, for example, a mixture or a solution, there is a plurality of such polyalkoxylated nucleic acid molecules present rather than a single molecule only. In other words, preferably the term a polyalkoxylated nucleic acid molecule is indicative of the genus of the molecule rather than its number.

It is also within the present invention that when it is referred to a non-polyalkoxylated nucleic acid molecule which is present or contained in, for example, a mixture or a solution, there is a plurality of such non-polyalkoxylated nucleic acid molecules present rather than a single molecule only. In other words, preferably the term a non-polyalkoxylated nucleic acid molecule is indicative of the genus of the molecule rather than its number.

In an embodiment of the present invention the nucleic acid moiety of the polyalkoxylated nucleic acid molecule is an aptamer. In an embodiment of the present invention the nucleic acid moiety of the polyalkoxylated nucleic acid molecule is a spiegelmer. In a further embodiment of the present invention the nucleic acid moiety of the non-polyalkoxylated nucleic acid molecule is an aptamer. In an embodiment of the present invention the nucleic acid moiety of the non-polyalkoxylated nucleic acid molecule is a spiegelmer.

In a further embodiment of the present invention the nucleic acid moiety of the polyalkoxylated nucleic acid molecule is an aptamer and the nucleic acid moiety of the non-polyalkoxylated nucleic acid molecule is an aptamer.

In a further embodiment of the present invention the nucleic acid moiety of the polyalkoxylated nucleic acid molecule is an aptamer and the nucleic acid moiety of the non-polyalkoxylated nucleic acid molecule is different from an aptamer, preferably the nucleic acid moiety of the non-polyalkoxylated nucleic acid molecule is not active as an aptamer, more preferably does not have the aptamer characteristics of the nucleic acid moiety of the polyalkoxylated nucleic acid molecule. As preferably used herein aptamer characteristic refer to the binding characteristics of the aptamer to its target molecule expressed, for example, as $K_D$ value.

In a further embodiment of the present invention the nucleic acid moiety of the polyalkoxylated nucleic acid molecule is a spiegelmer and the nucleic acid moiety of the non-polyalkoxylated nucleic acid molecule is a spiegelmer.

In a further embodiment of the present invention the nucleic acid moiety of the polyalkoxylated nucleic acid molecule is a spiegelmer and the nucleic acid moiety of the non-polyalkoxylated nucleic acid molecule is different from a spiegelmer, preferably the nucleic acid moiety of the non-polyalkoxylated nucleic acid molecule is not active as a spiegelmer, more preferably does not have the spiegelmer characteristics of the nucleic acid moiety of the polyalkoxylated nucleic acid molecule. As preferably used herein spiegelmer characteristic refer to the binding characteristics of the spiegelmer to its target molecule expressed, for example, as $K_D$ value.

As preferably used herein an aptamer is a nucleic acid molecule which binds to its target molecule through bonds different from Watson-Crick base pairing, whereby the nucleic acid molecule consists of D-nucleotides. The generation of aptamers is, for example, described in EP 0 533 838.

As preferably used herein a spiegelmer is a nucleic acid molecule which binds to its target molecule through bonds different from Watson-Crick base pairing, whereby the nucleic acid molecule essentially consists of L-nucleotides. The generation of spiegelmers is, for example, described in WO 98/08856.

The methods of the present invention can be applied to polyalkoxylated nucleic acids containing natural sugar moieties, for example 2'-deoxyribonucleic acids (hereinafter "DNA") and ribonucleic acids (hereinafter "RNA") and nucleic acids containing modified sugar moieties, modified phosphate moieties, or modified nucleobases. The methods according to the present invention are not restricted to the natural stereoisomer of RNA and DNA. Also polyalkoxylated nucleic acids comprising mirror image DNA (L-DNA) or RNA (L-RNA) as well as sugar-, phosphate- or nucleotide-modified L-DNA or L-RNA as well as D/L-hybrid nucleic acid molecules and modifications thereof can be prepared by means of the methods according to the present invention. Modifications to the sugar moiety include the change of the ring size (e.g. furanose, hexose), replacement, introduction or removal of single ring atoms (e.g. carba sugars, aza sugar), replacement, introduction or removal of side chain groups or atoms (e.g. 2'-F, 2'OMe), replacement of the ring by acyclic or poly cyclic derivatives (e.g. unlocked nucleic acid, amino acid nucleic acid, locked nucleic acid, tricycle nucleic acid), orientation or position of the nucleobase (α-anomeric orientation, hexitol nucleic acid). The nucleic acid molecule may also consist of one or more natural or unnatural abasic moieties (e.g. tetrahydrofurane, ethylene glycol). Modified phosphate moieties include phosphorothioates, phosphorodithioates, alkylphosphonates, alkylphosphates, phosphoramidates and phosphorthioamidates. Modifications of the nucleobases can be naturally occurring such as isonine, xanthine, 5,6-dihydrouracil or 5-methylcytosine or artificial modifications such as C5-alkynylpyrimidines, N-alkylated purines and pyrimidines, C6-derivatives of pyrimidines and purines and others. The nucleic acid molecule may also comprise or consist of one or more of the above modifications.

Methods for the assembly and synthesis of a nucleic acid molecule are well known in the art each of which may be used in the preparation of a nucleic acid molecule which is subject to the methods of the present invention. In many embodiments the nucleic acid molecule will be assembled by the phosphoramidite method employing a stepwise coupling of protected building blocks to the nascent nucleic acid molecule on a solid support (Beaucage et. al., *Tetrahedron* 1992, 48(12), 2223-2311). In a preferred embodiment synthesis direction is from 3' to 5' direction, but also reverse synthesis from 5' to 3' direction may be used (Srivastava et. al. *Nucleic Acids Symposium Series* 2008, 52, 103-104). Once the desired nucleic acid sequence has been assembled and all necessary modifications for downstream processing have been introduced, the nucleic acid molecule is cleaved from the solid support and deprotected. The nucleic acid molecule may then be purified by any means known in the art insofar.

Commonly, the cleavage and deprotection step involves the usage of ammonia and/or alkylamine or ammonia salts. For example, RNA is cleaved with $NH_3$/$MeNH_2$ followed by $NEt_3$.HF or $Bu_4NF$. In case of the using NHS-ester mediated polyalkoxylation, these amines and ammonia salts have to be removed prior to polyalkoxylation as they lead to unwanted side reactions lowering the coupling efficacy during polyalkoxylation. The removal of amine species is achieved by salt exchange which can be done by adding large quantities of sodium salts followed by Precipitation or ultrafiltration, or during IEX-HPLC using sodium salt gradients for elution. After IEX-HPLC purification the removal of excess salt is also necessary. Other types of conjugation reactions may or may not be as sensitive towards the presence of amines. A plurality of different techniques can be used for such purpose if necessary. In preferred embodiments salt exchange followed by ultrafiltration is used. The amino modified nucleic acid molecules used in the examples to illustrate the present invention were synthesized and purified according to examples 1-11.

Methods for the polyalkoxylation are well known in the art. Polyalkoxylates which can be used in the practicing of the methods of the present invention include, but are not limited to poly(ethylene oxides), polypropylene oxides) and mixed poly(ethylene oxide)/poly(propylene oxide) compounds. The polyalkoxylates are preferably of the formula:

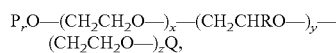

wherein x, y and z are independently zero or positive integers, provided that at least one of x, y and z is not zero; R is H or an alkyl, such as a C1-4 alkyl, particularly a methyl, group, $P_r$ is a capping group or a labelling group, and Q is a group permitting coupling with the oligonucleotide. When x, y or z are not zero, they are typically up to 1000. In some embodiments, x is from 3 to 1000, preferably from 100 to 500, and both y and z are zero. In other embodiments, x and y are each and independently from 3 to 1000, preferably from 100 to 500, and z is zero. In yet other embodiments, x and z are each and independently from 3 to 500, preferably from 100 to 300, and y is from 3 to 1000, preferably from 100 to 500. Preferably, the polyalkyleneoxide is capped, for example by a C1-4 alkyl group, preferably a methyl, group. Labelling groups which may be represented by $P_r$ include, but are not limited to fluorescein and biotin or also other reactive groups such as amine, thiol, maleimide, azide or alkyne. The polyalkoxylate compounds used in the practicing of the present invention are typically identified by their approximate average molecular weight and abbreviated chemical name (for example PEG=poly(ethylene glycol); PPG=poly(propylene glycol). The polyalkyleneoxide may be linear or branched, and typically has an average molecular weight of from 0.2 kD to 60 kD, preferably from 2 kD to 40 kD. When the polyalkyleneoxide is branched, the group, Q, permitting coupling with the nucleic acid molecule may carry two or more polyalkyleneoxide chains or moieties. For example, Q may represent a lysine or equivalent moiety carrying two polyalkyleneoxide chains or moieties, and a reactive group. Preferably, the polyalkoxylate is PEG.

A broad variety of suitable conjugation reactions can be used so as to couple the nucleic acid molecule to the polyalkoxylate. Typically, a nucleic acid molecule a possessing an amino, a thio, an azido or an alkyne modification is reacted with a polyalkoxylate that is modified with a suitable reactive group such as a carboxylic acid, a carboxylic acid ester, an aldehyde, an iodoalkyl group, a maleimide, an azide or an alkyne. The methods of the present invention are not limited to any polyalkoxylation method. Rather, the methods of the present invention may use the reaction product of any polyalkylation method. Preferably an amino-modified oligonucleotide is reacted with a polyalkoxylate-NHS-ester as a reactive group. The position of the amino-modification in the nucleic acid molecule can be on the 3'-end and/or at the 5'-end and/or internally, i.e. any nucleotide different from the 5'-terminal nucleotide and the 3'-terminal nucleotide. FIG. 2 illustrates in a non-limiting way a set of reagents that can be used to introduce such reactive amino-group into the nucleic acid molecule. Reaction of an amino-modified nucleic acid molecule with a polyalkoxylate N-hydroxysuccinimide ester (polyalkoxylate NHS ester) is typically performed in an aqueous organic solvent comprising water and a water miscible organic solvent. Preferred organic solvents are aprotic, polar and include, for example, DMF, DMSO, NMP and acetonitrile. The concentration of the organic solvent can vary from 10% to 50%, preferably % by weight. The nucleic acid molecule is preferably used in an aqueous solution such as a buffer, such as, e.g., sodium bicarbonate or sodium borate, however, also tertiary amines, such as $NEt_3$ or DIPEA in aqueous solution can be used. Preferably, the pH of the nucleic acid containing solution is adjusted to 8.5 to 9.5. The polyalkoxylate is used as and, respectively, provided in a solution in a water miscible organic solvent and remains in solution when added to the aqueous oligonucleotide. Mole ratios of the polyalkoxylate towards the oligonucleotide can vary from 1:1 to 5:1 per reactive amino group depending on scale and reactivity as will be acknowledged by a person skilled in the art. Addition of the polyalkoxylate preferably continues until completion of the reaction. The reaction can be followed by any means available to the skilled person. In many embodiments RP-HPLC is used for monitoring the polyalkoxylation reaction. To achieve best conversion, temperatures varying from ambient temperature such as 20° C., 21° C. or 22° C. to 45° C. can be used.

One aspect of the present invention is related to the polyalkoxylation reaction of an amino-modified nucleic acid molecule with a polyalkoxylate-NHS ester to form a polyalkoxylated nucleic acid molecule. NHS esters are reactive groups which not only react with an amino group of a nucleic acid molecule to form the desired product, but also react with water. Therefore, it is preferred to reduce the amount of water present in such reaction. However, water is necessary for dissolving the nucleic acid molecule and providing high concentration of the nucleic acid to achieve fast and complete reaction. On the other hand, polyalkoxylates are less soluble in water than in polar solvents such as DMF. Surprisingly, it has been found that the water content in such reactions can be significantly reduced if a quaternary ammonium compound such as $Bu_4NBr$ is added to the nucleic acid molecule prior to adding the polyalkoxylate in DMF. The total content of DMF equaled 76%, preferably by weight, while maintaining high nucleic acid concentration. Thus, side-reactions such as hydrolysis of the alkoxylate NHS ester are reduced and product conversion is enhanced as illustrated by examples 12-22.

After the reacting the polyalkoxylate and the nucleic acid molecule to form the conjugated polyalkoxylated nucleic acid molecule, the product is preferably separated from any unreacted oligonucleotide.

In accordance with the present invention it has surprisingly been found that a polyalkoxylated nucleic acid can be separated from a mixture of nucleic acid molecules comprising the polyalkoxylated nucleic acid molecule and a non-polyalkoxylated nucleic acid molecule very efficiently and with high product recovery by subjecting the crude polyalkoxylation reaction mixture to a precipitation step. In an embodiment precipitation is achieved by addition of a precipitating agent and leads to the formation of a suspension consisting of an amorphous or micro-crystalline solid and mother liquor. In an embodiment, a precipitating agent for oligonucleotides can be a water miscible organic solvent, a salt or an agent that changes the pH of the oligonucleotide solution. In an alternative embodiment, precipitation is achieved by cooling of an oligonucleotide solution such as the mixture of nucleic acid molecules subject to the methods of the present invention. A combination of precipitating agents can be used as well as the combination of cooling and adding one or several precipitating agents. In a preferred embodiment, the addition of at least one precipitating agent and/or cooling to/of crude polyalkoxylation reactions leads to precipitation of polyalkoxylated nucleic acid molecules, while unreacted oligonucleotides, i.e. non-polyalkoxylated nucleic acid molecules are or remain dissolved in the supernatant. Subsequent product harvest can easily be achieved by any solid-fluid separation technique known in the art. Such separation techniques preferably exploit the differences in the density of the substance mixture. For example the precipitate can be sedimented by gravity or centrifugation at 200-20,000 g. After sedimentation or centrifugation, the supernatant can be decanted and the precipitate can be collected. The subsequent product harvest can also exploit and thus be based on the particle size of the solid contained in a solid-fluid mixture. For example, the precipitate can be collected by filtration. Filtration is achieved by interposing a medium through which only the fluid can pass. Surface filters with or without the use of filter papers can be used, e.g. glass disc filters, büchner funnels, belt filters or rotary vacuum-drum filters. Certain filter aids may be used to aid filtration. Such filter aids are often incompressible diatomaceous earth, kieselguhr or perlite. Wood cellulose may also be used. Fluids flow through a filter from a high pressure side to a low pressure side of the filter. The simplest method to achieve this is by gravity. In a preferred embodiment, pressure in the form of compressed air or gas on the feed side (or vacuum on the filtrate side) is applied to make the filtration process faster. Alternatively, the liquid may flow through the filter by the force exerted by a pump.

The purification process, i.e. the method for preparing a polyalkoxylated nucleic acid molecule making use of a precipitation step according to the present invention is extremely beneficial, as it is a separation process, which is as powerful as a RP- or IEX-purification prior to the polyalkoxylation but is performed fast with cheap reagents and avoids the disadvantages of alternative methods described in the art such as in WO 2007/066069. WO 2007/066069 describes a method which exploits the increase of molecular weight due to polyalkoxylation to facilitate separation of a polyalkoxylated nucleic acid molecule from a non-polyalkoxylated nucleic acid molecule by ultrafiltration. However, oligonucleotides possessing a three dimensional structure stabilized by internal base pairing, such as aptamers and spiegelmers, tend to form aggregates of unreacted and polyalkoxylated nucleic acid molecules. Therefore, WO 2007/066069 suggests applying denaturing conditions. More specifically, 1 M $NaClO_4$ is to be added to the product and heat is to be applied to facilitate strand separation. Excess polyalkoxylate is subsequently removed by an IEX-HPLC polishing step. Sodium perchlorate, however, is a strong oxidation reagent. Together with heating there is an increased risk that the polyalkoxylated nucleic acid molecule might undergo oxidative degradation which is typically affecting its therapeutic use. In contrast thereto, the present invention proves to be superior as neither aggressive reagents are to be added to the reaction nor does heat have to be applied thereto. The harvested product is ready for subsequent IEX-HPLC polishing and removal of excess polyalkoxylate.

Insofar, it is specifically referred to FIG. 3A shows the IEX-HPLC analysis of typical crude synthesis product of 5'$NH_2$—NOX-E36 prior to PEGylation (1 prePEG, see Example 34). According to the chromatogram the crude product contained 58% full length product. The PEGylation of 1-prePEG led to the conversion to NOX-E36-40 kDaY-PEG (1), as indicated by IEX-HPLC-analysis (FIG. 3B). YPEG is a Y-shaped, branched PEG of 40 kDa. The addition of 10-fold excess of MeOH and subsequent cooling to −20° C. led to the formation of a precipitate (example 23). The precipitate was collected by centrifugation followed by decantation and the precipitate and supernatant were analyzed by IEX- and RP-HPLC. RP-HPLC indicated that the PEGylated product NOX-E36-40 kDaYPEG (1) is found almost exclusively in the precipitate (FIG. 3C). Only very minor amounts of 1 are found in the supernatant (FIG. 3D). IEX-HPLC analysis of the precipitate shows 68% purity of the product (FIG. 3E), while the supernatant only contained a broad variety of unconjugated oligonucleotide related impurities (FIG. 3F). Subsequent IEX polishing and PEG removal was conducted with high product recovery and high product purity.

The purification method according to the present invention, i.e. the method of the present invention for preparing a polyalkoxylated nucleic acid molecule using a precipitation step, also allows for the purification of a polyalkoxylated nucleic acid molecule prepared from very poor crude solid-phase synthesis products. A synthesis run was deliberately performed with insufficient amount of phosphoramidites leading to crude 5'NH$_2$.NOX-E36 with a purity of 27% FLP (full length polymer or product) (example 5). Even this synthesis product could be PEGylated (example 14) and purified in an efficient way (example 24).

The precipitation according to the present invention can not only be initiated by addition of MeOH and subsequent cooling to −20° C. (examples 23, 24 and 37) but also by cooling only without prior co-solvent addition to 4° C. (examples 38 and 39) or −20° C. (example 40)

The purification method according to the present invention is not restricted to oligonucleotide conjugates to 40 kDaYPEG. A broad variety of nucleic acids was modified with PEG-species of different length and PEG-load (10 kDa-2×40 kDa) and all resulting conjugates were easily purified by Precipitation (example 23-28). In addition, the purification process is not restricted to the nature of the oligonucleotide. Purification of DNA as well as RNA of different length is demonstrated in examples 29-33.

It is within the present invention that a nucleic acid is a nucleic acid molecule. Insofar the terms nucleic acid and nucleic acid molecule are used herein in a synonymous manner if not indicated to the contrary. Moreover, such nucleic acid(s) is/are preferably also referred to herein as the nucleic acid molecule(s) according to the present invention, the nucleic acid(s) according to the present invention, the inventive nucleic acid(s) or the inventive nucleic acid molecule(s). Additionally, it is within the present invention that a nucleic acid is an oligonucleotide.

It will be acknowledged by the ones skilled in the art that the nucleic acid in accordance with the invention preferably consists of nucleotides which are covalently linked to each other, preferably through phosphodiester links or linkages.

BRIEF DESCRIPTION OF THE DRAWINGS

The present invention is further illustrated by the following tables, figures and examples from which further features, embodiments and advantages may be taken, wherein

FIG. 8 shows Table 1 indicating the sequence of nucleic acids used to demonstrate the process according to the present invention.

EXAMPLE 1

RNA-Synthesis

Figure 1:
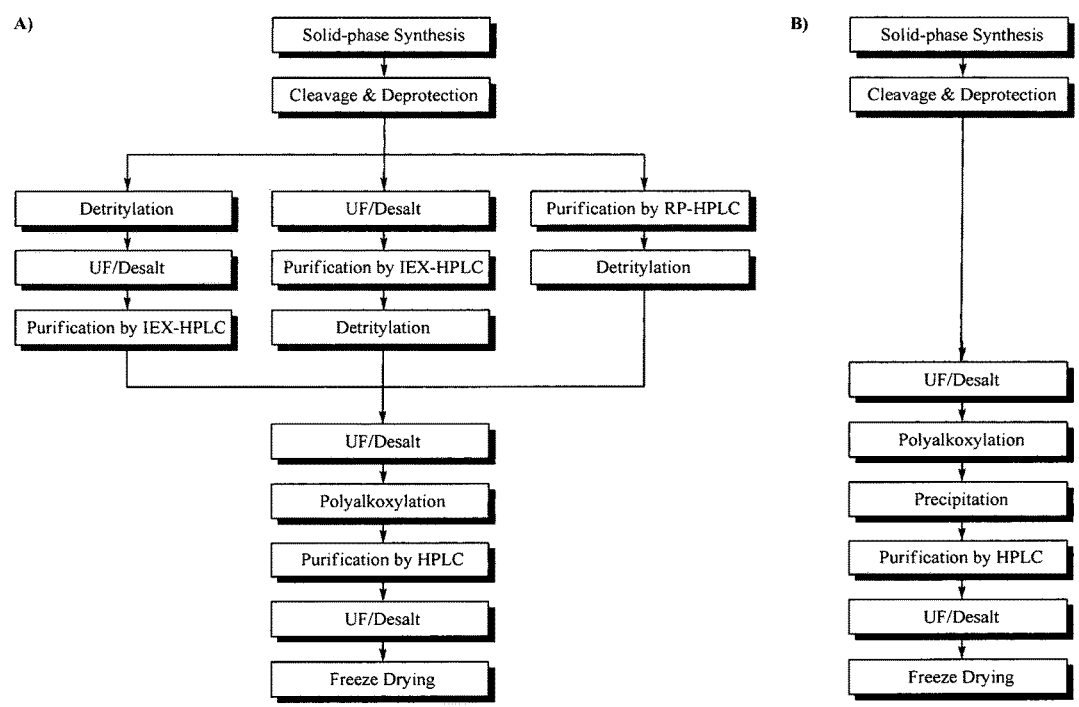
FIG. 1A shows a schematic drawing of a typically applied process for the production of polyalkoxylated nucleic acids.
FIG. 1B shows a schematic drawing of a process according to the present invention.
Figure 2:
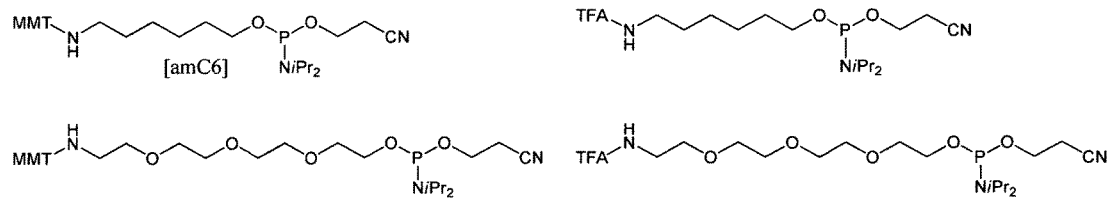
FIG. 2 shows reagents enabling for the introduction of reactive amino-groups into the nucleic acids.
Figure 2:
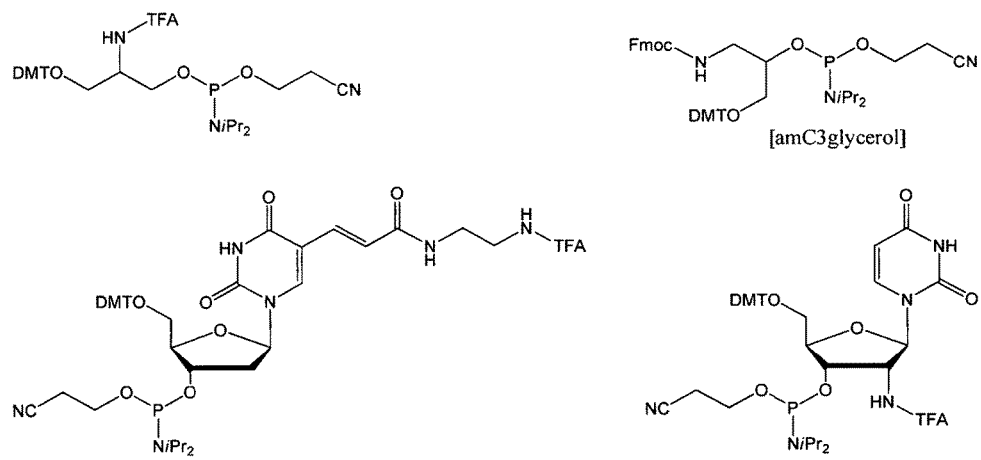
Figure 2:
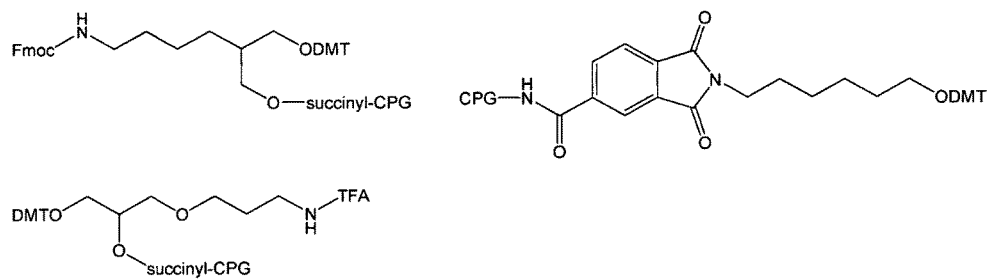
Figure 3:
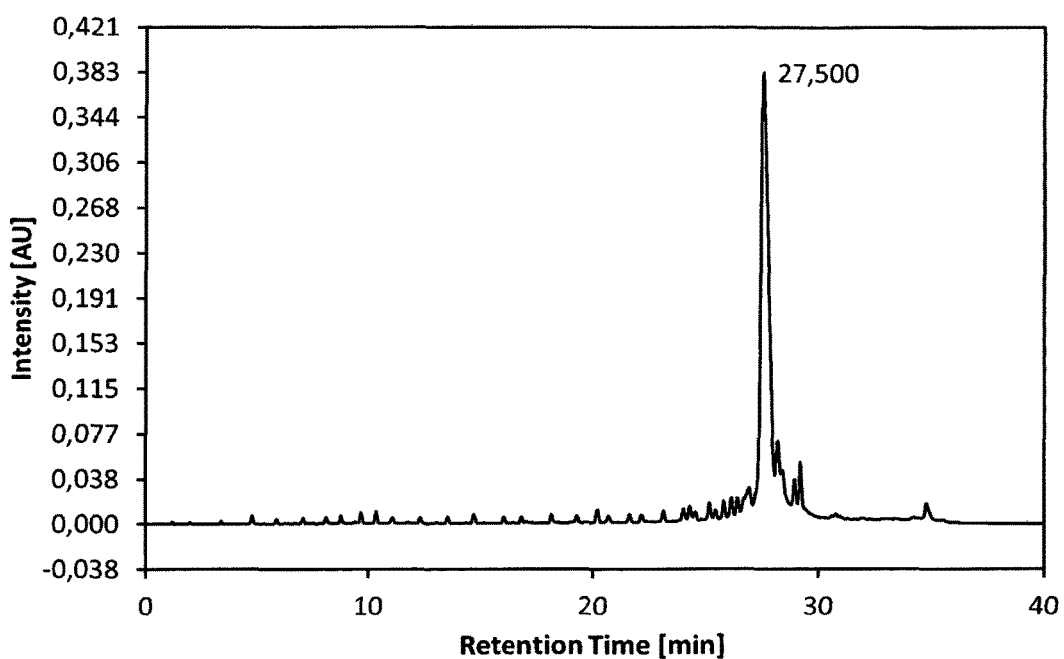
FIG. 3A shows the IEX-HPLC analysis of typical crude synthesis product of 5'NH$_2$—NOX-E36 prior to PEGylation (example 4)
FIG. 3B shows the IEX-HPLC analysis of typical crude synthesis product of 5'NH$_2$—NOX-E36 after PEGylation (example 13)
FIG. 3C shows the RP-HPLC analysis the precipitate after precipitation of a typical conjugation reaction of 5'-NH$_2$—NOX-E36 and 40 kDaYPEG (example 23)
FIG. 3D shows the RP-HPLC analysis the supernatant after precipitation of a typical conjugation reaction of 5'-NH$_2$—NOX-E36 and 40 kDaYPEG (example 23)
FIG. 3E shows the IEX-HPLC analysis the precipitate after precipitation of a typical conjugation reaction of 5'-NH$_2$—NOX-E36 and 40 kDaYPEG (example 23)
FIG. 3F shows the IEX-HPLC analysis the supernatant after precipitation of a typical conjugation reaction of 5'-NH$_2$—NOX-E36 and 40 kDaYPEG (example 23)
Figure 3:
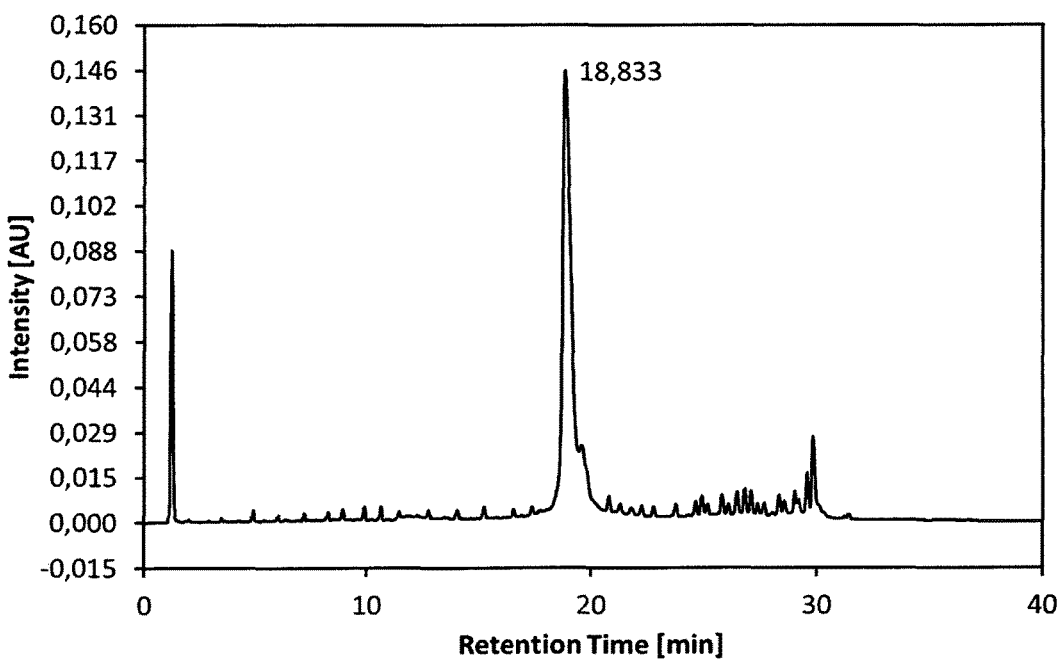
Figure 4:
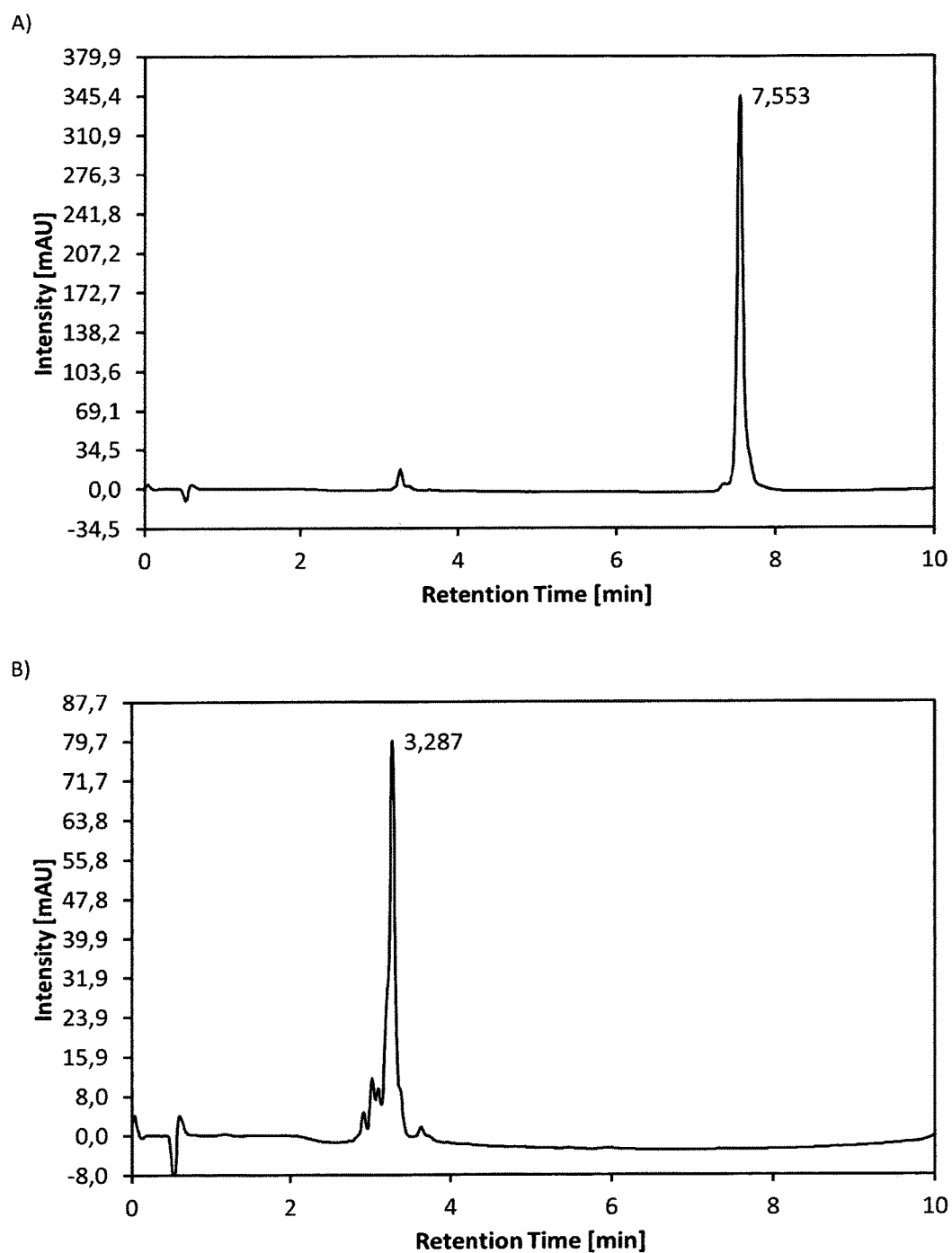
FIG. 4A shows the RP-HPLC analysis the precipitate after precipitation of a typical conjugation reaction of 5'-NH$_2$—NOX-E36 and 40 kDaYPEG (example 37)
FIG. 4B shows the RP-HPLC analysis the supernatant after precipitation of a typical conjugation reaction of 5'-NH$_2$—NOX-E36 and 40 kDaYPEG (example 37)
FIG. 4C shows the IEX-HPLC analysis the precipitate after precipitation of a typical conjugation reaction of 5'-NH$_2$—NOX-E36 and 40 kDaYPEG (example 37)
FIG. 4D shows the IEX-HPLC analysis the supernatant after precipitation of a typical conjugation reaction of 5'-NH$_2$—NOX-E36 and 40 kDaYPEG (example 37)
Figure 5:
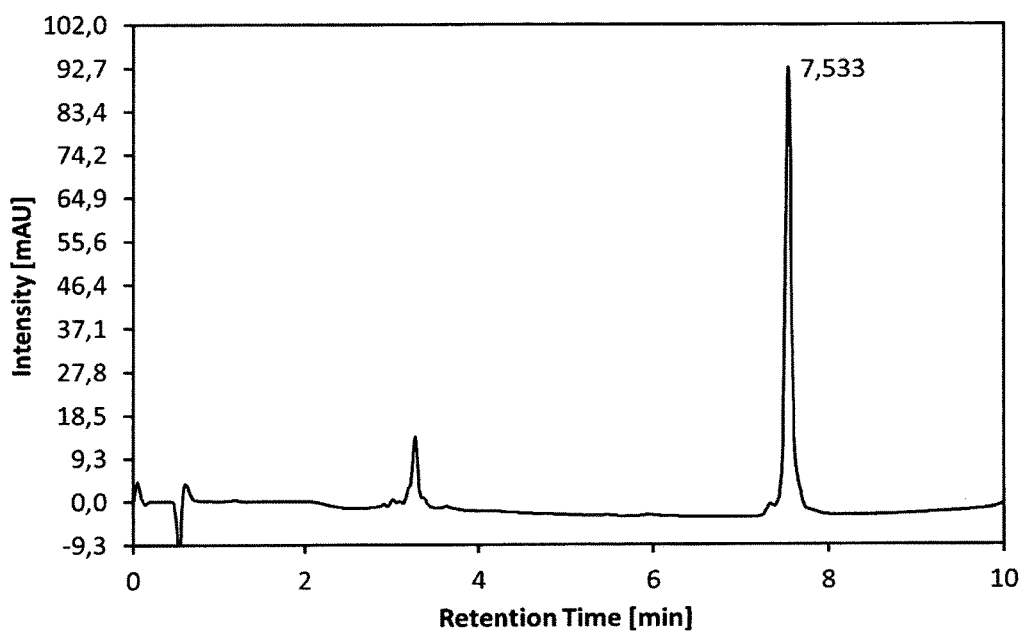
FIG. 5A shows the RP-HPLC analysis the precipitate after precipitation of a typical conjugation reaction of 5'-NH$_2$—NOX-E36 and 40 kDaYPEG (example 38)
FIG. 5B shows the RP-HPLC analysis the supernatant after precipitation of a typical conjugation reaction of 5'-NH$_2$—NOX-E36 and 40 kDaYPEG (example 38)
FIG. 5C shows the IEX-HPLC analysis the precipitate after precipitation of a typical conjugation reaction of 5'-NH$_2$—NOX-E36 and 40 kDaYPEG (example 38)
FIG. 5D shows the IEX-HPLC analysis the supernatant after precipitation of a typical conjugation reaction of 5'-NH$_2$—NOX-E36 and 40 kDaYPEG (example 38)
Figure 5:
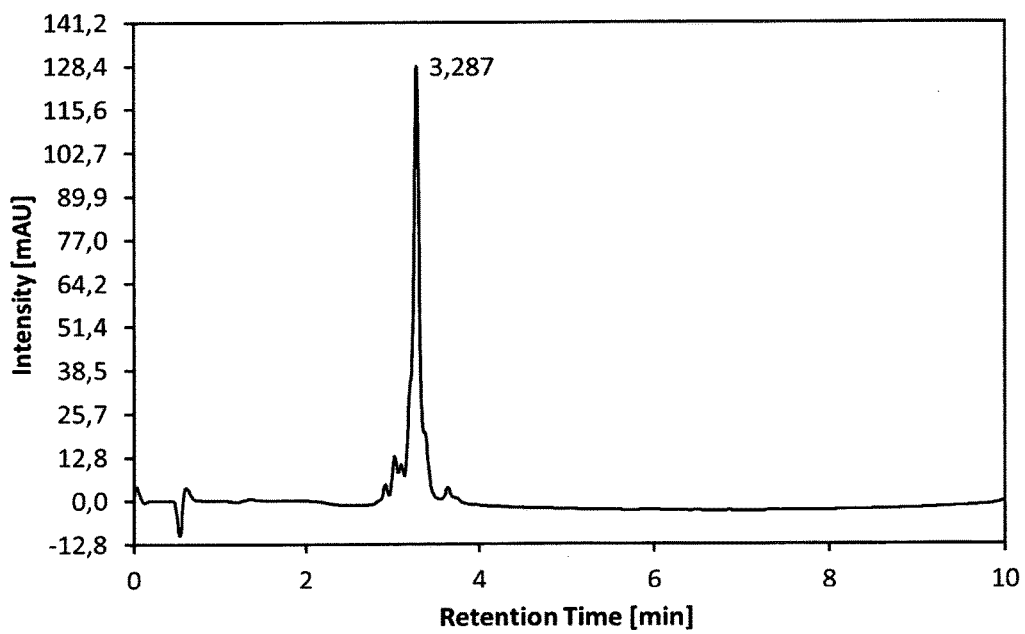
Figure 6:
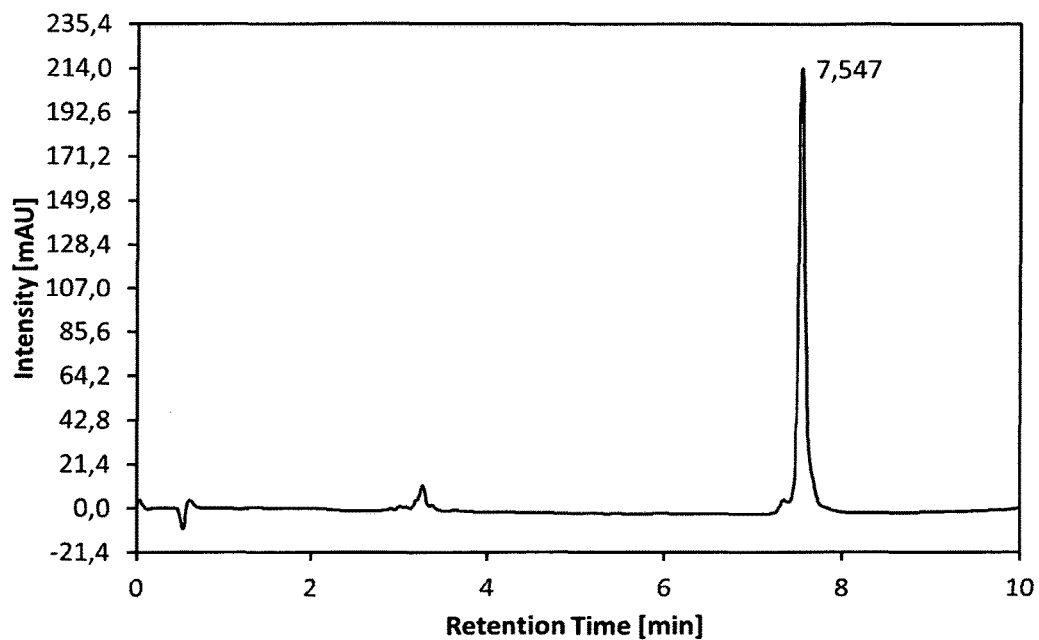
FIG. 6A shows the RP-HPLC analysis the precipitate after precipitation of a typical conjugation reaction of 5'-NH$_2$—NOX-E36 and 40 kDaYPEG (example 39)
FIG. 6B shows the RP-HPLC analysis the supernatant after precipitation of a typical conjugation reaction of 5'-NH$_2$—NOX-E36 and 40 kDaYPEG (example 39)
FIG. 6C shows the IEX-HPLC analysis the precipitate after precipitation of a typical conjugation reaction of 5'-NH$_2$—NOX-E36 and 40 kDaYPEG (example 39)
FIG. 6D shows the IEX-HPLC analysis the supernatant after precipitation of a typical conjugation reaction of 5'-NH$_2$—NOX-E36 and 40 kDaYPEG (example 39)
Figure 6:
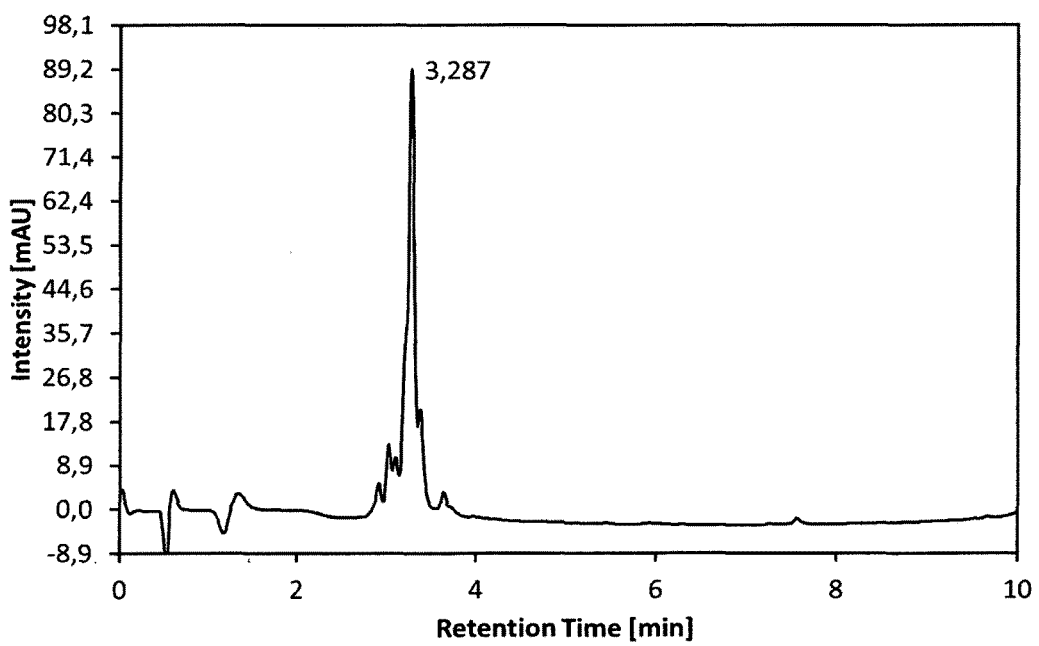
Figure 7:
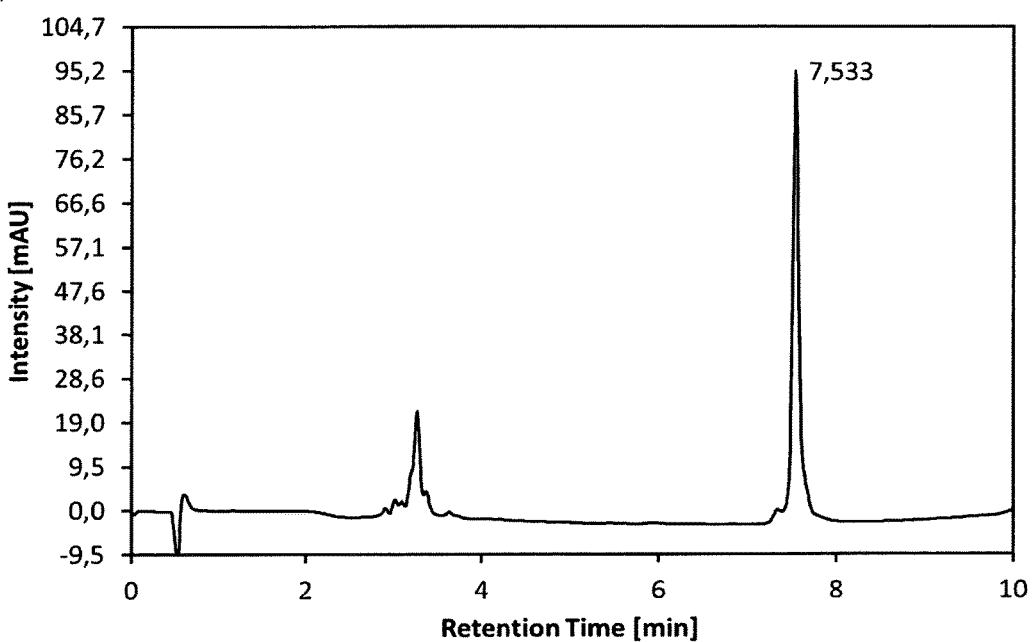
FIG. 7A shows the RP-HPLC analysis the precipitate after precipitation of a typical conjugation reaction of 5'-NH$_2$—NOX-E36 and 40 kDaYPEG (example 40)
FIG. 7B shows the RP-HPLC analysis the supernatant after precipitation of a typical conjugation reaction of 5'-NH$_2$—NOX-E36 and 40 kDaYPEG (example 40)
FIG. 7C shows the IEX-HPLC analysis the precipitate after precipitation of a typical conjugation reaction of 5'-NH$_2$—NOX-E36 and 40 kDaYPEG (example 40)
FIG. 7D shows the IEX-HPLC analysis the supernatant after precipitation of a typical conjugation reaction of 5'-NH$_2$—NOX-E36 and 40 kDaYPEG (example 40)
Figure 7:
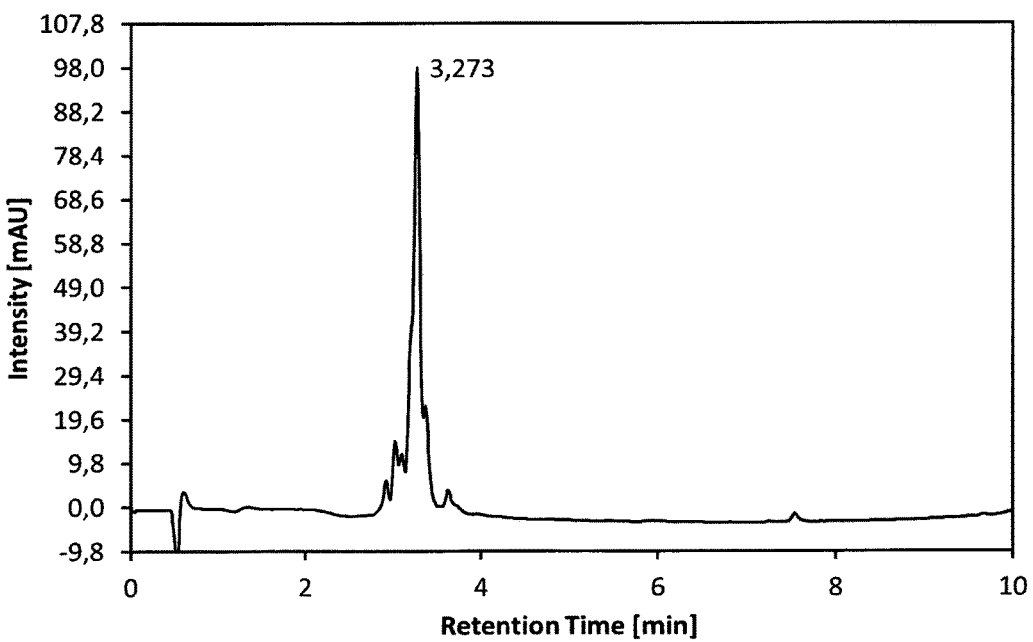

Spiegelmers were produced by solid-phase synthesis with an ÄktaPilot100 synthesizer (GE Healthcare, Freiburg) in a 6.3 mL fixed volume column using 2'TBDMS RNA phosphoramidite chemistry (Damha and Ogilvie, *Methods in Molecular Biology*, 1993, 81-114, The Humana Press Inc., Totowa, N.J.). L-rA(N-Bz)-, L-rC(Ac)-, L-rG(N-ibu)-, and L-rU- phosphoramidites were purchased from Proligo-SAFC (Hamburg, D). The 5'-amino-modifier was purchased from ChemGenes (Wilmington, Mass., USA). Synthesis of the amino-modified spiegelmer was started on L-riboG, or L-riboC modified. CPG pore size 600 Å (Prime Synthesis, Aston, Pa., USA), or alternatively on 3'amino(TFA) modified CPG pore size 1000 Å (ChemGenes, Wilmington, Mass., USA). For coupling (12 min per cycle), 0.6 M ethylthiotetrazole (Azide Chemical Co., Ltd, Anzhen, Wuxi, CN) in acetonitrile, and 1.5-4 equivalents of the respective 0.2 M phosphoramidite solution in acetonitrile was used. An oxidation-capping-oxidation cycle was used. Standard solvents and reagents for oligonucleotide synthesis were purchased from Biosolve (Valkenswaard, NL). Proligo (Hamburg, D), VWR (Karlsruhe, D)) or Sigma Aldrich (Taufkirchen, D). The spiegelmers were synthesized 5'-MMT-ON. Cleavage and deprotection was achieved according to Wincott et al. (Wincott, *Nucleic Acids Research* 1995, 23(14), 2677-2684) with minor alterations. In detail, upon completion of the automated synthesis, the CPG-bound oligonucleotide (50-150 μmol) was briefly dried and transferred into a glass bottle. 80 mL of aq. $MeNH_2$ (40%) were added, and the suspension was gently agitated at room temperature. After 90 min the slurry was filtered and the residual CPG washed several times with aq. EtOH (50%). The combined filtrates were concentrated and finally lyophilized to dryness. For the removal of the 2'TBDMS groups, the dry crude product was dissolved in 15 mL DMSO followed by 7.5 mL $NEt_3$ and 10 mL $n-NEt_3.3HF$. This mixture was gently agitated at 65° C. for 2 h. After cooling to room temperature, 120 mL n-BuOH was added and the resulting precipitate was collected and washed with acetone. For cleavage of the 5'MMT-group, the resulting crude product was dissolved in water and 20 mL acetic acid was added. After 30 min at 40° C. RP-HPLC showed complete MMT removal and 65 mL of 5M NaOH solution was added under stirring for neutralisation. Subsequently the spiegelmer was desalted by tangential-flow filtration using a 5 K regenerated cellulose membrane (Millipore, Bedford, Mass.). Subsequently, 0.4 of 0.25M NaCl solution was added and the solution was again desalted by tangential-flow filtration. Finally the product was harvested and dried by lyophilization.

EXAMPLE 2

RNA-Synthesis

Spiegelmers were also produced by solid-phase synthesis in a 48 mL fixed volume column analogously to Example 1 with the following alterations. For cleavage and deprotection 200 mL $MeNH_2$ (40%), 120 mL DMSO, 60 mL $NEt_3$ and 80 mL $NEt_3.3HF$ were used. After Cleavage of the 2'TBDMS groups, the reaction was quenched by addition 1 of ice water and removal of the MMT was assisted by addition of acetic acid (25 mL). Subsequently the spiegelmer was desalted by tangential-flow filtration using a 2 K regenerated cellulose membrane (Satorius, Göttingen, D), 3 of 0.25M NaCl solution were added for the salt exchange and then again the solution was desalted by tangential-flow filtration.

EXAMPLE 3

DNA-Synthesis

DNA-Aptamers and DNA-spiegelmer were synthesized similar to example 1 with the following alterations. The used D-dA(N-Bz)-, D-dC(Ac)-, D-dG(N-ibu)-, and D-dT-phosphoramidites were purchased from Proligo (Hamburg, D), the corresponding L-amidites and CPGs (D-dG and L-dT, 1000 Å) were purchased from ChemGenes (Wilmington, Mass., USA). For coupling (8 min per cycle), 0.6 M ethylthiotetrazole (Azide Chemical Co., Ltd,

EXAMPLE 4

SYNTHESIS of 5'$NH_2$—NOX-E36 (1 prePEG)

Applying the procedure described in Example 1, 1.11 g L-rG CPG (600 Å, 70 mol/g, 78 μmol) were used to assemble 5'$NH_2$—NOX-E36 (1 prePEG) with 3 Eq. of amidite per nucleotide coupling cycle. Yield: 7077 OD, Purity: 54%, Mass: 12966, (calc.: 12996).

EXAMPLE 5

Synthesis of 5'$NH_2$—NOX-E36 (1 prePEG)

Applying the procedure described in Example 2, 9.43 g L-rG CPG (600 Å, 70 μmol/g, 660 μmol) were used to assemble 5'$NH_2$—NOX-E36 (1 prePEG) with 1.66 Eq. of amidite per nucleotide coupling cycle. Yield: 68600 OD, Purity: 27%, Mass: 12967, (calc.: 12996).

EXAMPLE 6

Synthesis of 5'$(NH_2)_2$—NOX-E36 (4 prePEG)

Applying the procedure described in Example 1, 1.11 g L-rG CPG (600 Å, 70 μmol/g, 78 μmol) were used to assemble 5'$(NH_2)_2$—NOX-E36 (4 prePEG) with 3 Eq. of amidite per nucleotide coupling cycle. Yield: 10652 OD, Purity: 38% FLP, Mass: 13148, (calc.: 13149).

EXAMPLE 7

Synthesis of 5'$NH_2$—NOX-A12 (5 prePEG)

Applying the procedure described in Example 1, 1.97 g L-rC CPG (600 Å, 72 μmol/g, 142 μmol) were used to assemble 5'$NH_2$—NOX-A12 (5 prePEG) with 2.5 Eq. of amidite per nucleotide coupling cycle. Yield: 22012 OD, Purity: 43% FLP, Mass: 14656, (calc.: 14657).

EXAMPLE 8

Synthesis of 5'$NH_2$—NOX-1194 (6 prePEG)

Applying the procedure described in Example 1, 1.90 g L-rC CPG (600 Å, 72 μmol/g, 137 μmol) were used to assemble 5'$NH_2$—NOX—H94 (6 prePEG) with 2.5 Eq. of amidite per nucleotide coupling cycle. Yield: 26880 OD, Purity: 33% FLP, Mass: 14605, (calc.: 14602).

EXAMPLE 9

Synthesis of 5'$NH_2$—NOX-A14 (7 prePEG)

Applying the procedure described in Example 1, 1.96 g L-rC CPG (600 Å, 72 μmol/g, 141 μmol) were used to assemble 5'$NH_2$—NOX-A14 (7 prePEG) with 2.5 Eq. of amidite per nucleotide coupling cycle. Yield: 17028 OD (681 mg), Purity: 60% FLP IEX, Mass: 9628, (calc.: 9628).

EXAMPLE 10

Synthesis of 5'NH$_2$—NOX-G12 (8 prePEG)

Applying the procedure described in Example 3, 1.80 g L-dT CPG (1000 Å, 36 µmol/g, 64.5 µmol) were used to assemble 5'NH$_2$—NOX-G12 (8 prePEG) with 3 Eq. of amidite per nucleotide coupling cycle. Yield: 12141 OD (401 mg), Purity: 66% FLP IEX, Mass: 14533, (calc.: 14529).

EXAMPLE 11

Synthesis of 5'NH$_2$-TBA (9 prePEG)

Applying the procedure described in Example 3, 1.73 g D-dG CPG (1000 Å, 37 µmol/g, 64.0 µmol) were used to assemble 5'NH$_2$-TBA (9 prePEG) with 2.5 Eq. of amidite per nucleotide coupling cycle. Yield: 6000 OD (198 mg), Purity: 77% FLP IEX, Mass: 4904, (calc.: 4905).

EXAMPLE 12

PEGylation Reaction

The amino-modified (deoxy-)oligonucleotide to be reacted was dissolved in water (1000 OD/mL). TBABr dissolved in DMF (3 eq. per phosphate of total oligonucleotide in DMF, 0.8 mL/mL oligonucleotide solution), DIPEA (75 µL/mL oligonucleotide solution) and PEG-NHS (Jen-Kem Technology, Allen, Tex., USA) dissolved in DMF (1.5 Eq with respect to full length product in DMF, 2.4 mL/mL oligonucleotide solution) was added successively to the oligonucleotide solution. The reaction mixture was agitated vigorously for 30 min and the reaction followed by RP-HPLC. If necessary, additional PEG-NHS was added neat to drive the reaction to completion. After complete conversion the reaction was stopped by addition of AcOH (80%, 37.5 µL/mL oligonucleotide solution).

EXAMPLE 13

Synthesis of NOX-E36-40 kDaPEG (1)

Applying the procedure described in Example 12, 7077 OD (283 mg, 54% FLP, 11.8 µmol) 5'NH$_2$—NOX-E36 (1 prePEG) were reacted with a total of 1.11 g (27.7 µmol) 40 kDaYPEG-NHS in the presence of 687 mg (2.13 mmol) Bu$_4$NBr, 531 µL (3.12 mmol) DIPEA in 30.1 mL DMF/H2O (3.25/1, v/v). Monitoring of the reaction by RP-HPLC showed 64% conversion.

EXAMPLE 14

Synthesis of NOX-E36-40 kDaPEG (1)

Applying the procedure described in Example 12, 100 OD (4 mg, 27% FLP, 83.1 nmol) 5'NH$_2$—NOX-E36 (1 prePEG) were reacted with a total of 5.6 mg (0.141 µmol) 40 kDaYPEG-NHS in the presence of 10.7 mg (33.1 µmol) Bu$_4$NBr, 7.5 µL (43.1 µmol) DIPEA in 4254 DMF/H2O (3.25/1, v/v). Monitoring of the reaction by RP-HPLC showed 32% conversion.

EXAMPLE 15

Synthesis of NOX-E36-20 kDaPEG (2)

Applying the procedure described in Example 12, 1000 OD (40 mg, 56% FLP, 1.72 µmol) 5'NH$_2$—NOX-E36 (1-prePEG) were reacted with a total of 51.7 mg (2.59 µmol) 20 kDaPEG-NHS in the presence of 107 mg (331 µmol) Bu$_4$NBr, 75 µL (431 µmol) DIPEA in 4.25 mL DMF/H2O (3.25/1, v/v). Monitoring of the reaction by RP-HPLC showed 64% conversion.

EXAMPLE 16

Synthesis of NOX-E36-10 kDaPEG (3)

Applying the procedure described in Example 12, 1000 OD (40 mg, 56% FLP, 1.72 µmol) 5'NH$_2$—NOX-E36 (1-prePEG) were reacted with a total of 75.9 mg (7.59 µmol) 10 kDaPEG-NHS in the presence of 107 mg (331 µmol) Bu$_4$NBr, 75 µL (431 µmol) DIPEA in 4.25 mL DMF/H2O (3.25/1, v/v). Monitoring of the reaction by RP-HPLC showed 61% conversion.

EXAMPLE 17

Synthesis of NOX-E36-2×40 kDaPEG (4)

Applying the procedure described in Example 12, 10642 OD (425 mg, 38% FLP, 12.3 µmol) 5'(NH$_2$)$_2$—NOX-E36 (4-prePEG) were reacted with a total of 1.23 g (86.0 µmol) 40 kDaYPEG-NHS in the presence of 761 mg (2.36 mmol) Bu$_4$NBr, 798 µL (4.69 mmol) DIPEA in 45.2 mL DMF/H2O (3.25/1, v/v). Monitoring of the reaction by RP-HPLC showed 44% conversion.

EXAMPLE 18

Synthesis of NOX-A12-40 kDaYPEG (5)

Applying the procedure described in Example 12, 21014 OD (840 mg, 43% FLP, 24.6 µmol) 5'NH$_2$—NOX-A12 (5-prePEG) were reacted with a total of 3.44 g (86.0 µmol) 40 kDaYPEG-NHS in the presence of 3.99 mg (12.4 mmol) Bu$_4$NBr, 1.58 mL (9.04 mol) DIPEA in 89.3 mL DMF/H2O (3.25/1, v/v). Monitoring of the reaction by RP-HPLC showed 68% conversion.

EXAMPLE 19

Synthesis of NOX—H94-40 kDaYPEG (6)

Applying the procedure described in Example 12, 25880 OD (840 mg, 33% FLP, 23.4 µmol) 5'NH$_2$—NOX—H94 (6-prePEG) were reacted with a total of 1.40 g (35.1 µmol) 40 kDaYPEG-NHS in the presence of 1.59 g (4.94 mmol) Bu$_4$NBr, 1.91 mL (11.1 mmol) DIPEA in 110 mL DMF/H2O (3.25/1, v/v). Monitoring of the reaction by RP-HPLC showed 30% conversion.

EXAMPLE 20

Synthesis of NOX-A14-40 kDaYPEG (7)

Applying the procedure described in Example 12, 16030 OD (641 mg, 60% FLP, 40.0 µmol) 5'NH$_2$—NOX-A14 (7-prePEG) were reacted with a total of 4.00 g (100 µmol)

40 kDaYPEG-NHS in the presence of 2.99 g (9.27 mmol) Bu$_4$NBr, 1.20 mL (6.90 mmol) DIPEA in 68.1 mL DMF/H2O (3.25/1, v/v). Monitoring of the reaction by RP-HPLC showed 80% conversion.

EXAMPLE 21

Synthesis of NOX-G12-40 kDaYPEG (8)

Applying the procedure described in Example 12, 11156 OD (446 mg, 66% FLP, 20.3 µmol) 5'NH$_2$—NOX-G12 (8-prePEG) were reacted with a total of 1.84 g (46.0 µmol) 40 kDaYPEG-NHS in the presence of 2.19 g (6.78 mmol) Bu$_4$NBr, 837 µL (4.92 mmol) DIPEA in 47.4 mL DMF/H2O (3.25/1, v/v). Monitoring of the reaction by RP-HPLC showed 64% conversion.

EXAMPLE 22

Synthesis of TBA-40 kDaYPEG (9)

Applying the procedure described in Example 12, 5000 OD (200 mg, 73% FLP, 29.8 µmol) 5'NH$_2$-TBA (9-prePEG) were reacted with a total of 2.45 g (61.2 µmol) 40 kDaY-PEG-NHS in the presence of 946 mg (2.94 mmol) Bu$_4$NBr, 375 µL (2.21 mmol) DIPEA in 21.3 mL DMF/H2O (3.25/1, v/v). Monitoring of the reaction by RP-HPLC showed 84% conversion.

EXAMPLE 23

Purification of Crude NOX-E36-40 kDaYPEG (1) by Precipitation

A sample of 100 OD (425 µL) of the material generated in Example 13 was transferred to a falcon tube, 4 mL MeOH were added. The mixture was thoroughly vortexed, and stored at −20° for 30 min. The resulting precipitate was spun down (4000 g), the supernatant was decanted. The combined organic phase was concentrated to dryness. Recovery precipitate: 65 OD, 92% pegylated species (RP-HPLC), 65% FLP (IEX); Recovery supernatant: 22 OD, 9% pegylated species (RP-HPLC), distribution of minor peaks (IEX).

EXAMPLE 24

Purification of Crude NOX-E36-40 kDaYPEG (1) by Precipitation

A sample of 1000 OD (4.25 mL) of the material generated in Example 13 was transferred to a falcon tube, 40 mL MeOH were added. The mixture was thoroughly vortexed, and stored at −20° for 30 min. The resulting precipitate was filtered of using a glass filter funnel (pore size 16-40 µm. The filtrate was concentrated to dryness. Recovery precipitate: 682 OD, 92% pegylated species (RP-HPLC), 63% FLP (IEX); Recovery supernatant: 243 OD, 2% pegylated species (RP-HPLC), distribution of minor peaks (IEX).

EXAMPLE 25

Purification of Crude NOX-E36-40 kDaYPEG (1) by Precipitation

A sample of 100 OD (425 µL) of the material generated in Example 14 was transferred to a falcon tube, and 4 mL MeOH were added. The mixture was thoroughly vortexed, and stored at −20° for 30 min. The resulting precipitate was spun down (4000 g), the supernatant was decanted. The combined organic phase was concentrated to dryness. Recovery precipitate: 34 OD, 81% pegylated species (RP-HPLC), 58% FLP (IEX); Recovery supernatant: 51 OD, 0% pegylated species (RP-HPLC), distribution of minor peaks (IEX).

EXAMPLE 26

Purification of Crude NOX-E36-20 kDaPEG (2) by Precipitation

A sample of 100 OD (425 µL) of the material generated in Example 15 was transferred to a falcon tube, and 4 mL MeOH were added. The mixture was thoroughly vortexed, and stored at −20° for 30 min. The resulting precipitate was spun down (4000 g), the supernatant was decanted. The combined organic phase was concentrated to dryness. Recovery precipitate: 62 OD, 92% pegylated species (RP-HPLC), 69% FLP (IEX); Recovery supernatant: 33 OD, 0% pegylated species (RP-HPLC), distribution of minor peaks (IEX).

EXAMPLE 27

Purification of Crude NOX-E36-10 kDaPEG (3) by Precipitation

A sample of 100 OD (425 µL) of the material generated in Example 16 was transferred to a falcon tube, and 4 mL MeOH were added. The mixture was thoroughly vortexed, and stored at −20° for 30 min. The resulting precipitate was spun down (4000 g), the supernatant was decanted. The combined organic phase was concentrated to dryness. Recovery precipitate: 68 OD, 96% PEGylated species (RP-HPLC), 70% FLP (IEX); Recovery supernatant: 36 OD, 0% PEGylated species (RP-HPLC), distribution of minor peaks (IEX).

EXAMPLE 28

Purification of Crude NOX-E36-2×40 kDaPEG (4) by Precipitation

Two 22.5 mL aliquots of the material generated in Example 17 (10642 OD, 38% FLP prior to PEGylation) were transferred into two 750 mL centrifuge bottles (Thermo Scientific Heraeus, Hanau, D), and 225 mL MeOH were added to each. The mixtures were thoroughly mixed, and stored at −20° for 2 hrs. The resulting precipitate was spun down (4000 g), the supernatant was decanted. The combined organic phase was concentrated to dryness. Recovery precipitate: 4230 OD, 95% PEGylated species (RP-HPLC), 53% FLP (IEX); Recovery supernatant: 6500 OD, 4% PEGylated species (RP-HPLC), distribution of minor peaks (IEX).

EXAMPLE 29

Purification of Crude NOX-A12-40 kDaYPEG (5) by Precipitation

Two 29.7 mL aliquots of the material generated in Example 18 were transferred into two 750 mL centrifuge bottles (Thermo Scientific Heraeus, Hanau, D), and 450 mL MeOH were added to each. The mixtures were thoroughly mixed, and stored at −20° for 2 hrs. The resulting precipitate was spun down (4000 g), the supernatant was decanted. The combined organic phase was concentrated to dryness. Recovery precipitate: 10604 OD, 95% PEGylated species (RP-HPLC), 58% FLP (IEX); Recovery supernatant: 4900 OD, 13% PEGylated species (RP-HPLC), distribution of minor peaks (IEX).

EXAMPLE 30

Purification of Crude NOX—H94-40 kDaYPEG (6) by Precipitation

Two 55 mL aliquots of the material generated in Example 19 were transferred into two 750 mL centrifuge bottles (Thermo Scientific Heraeus, Hanau, D), and 550 mL MeOH were added to each. The mixtures were thoroughly mixed, and stored at −20° for 2 hrs. The resulting precipitate was spun down (4000 g), the supernatant was decanted. The combined organic phase was concentrated to dryness. Recovery precipitate: 9048 OD, 77% PEGylated species (RP-HPLC), 45% FLP (IEX); Recovery supernatant: 15250 OD, 2% PEGylated species (RP-HPLC), distribution of minor peaks, 7% FLP (IEX).

EXAMPLE 31

Purification of Crude NOX-A14-40 kDaYPEG (7) by Precipitation

Two 34 mL aliquots of the material generated in Example 20 were transferred into two 750 mL centrifuge bottles (Thermo Scientific Heraeus, Hanau, D), and 350 mL MeOH were added to each. The mixtures were thoroughly mixed, and stored at −20° for 2 hrs. The resulting precipitate was spun down (4000 g), the supernatant was decanted. The combined organic phase was concentrated to dryness. Recovery precipitate: 11791 OD, 92% PEGylated species (RP-HPLC), 51% FLP (IEX); Recovery supernatant: 2350 OD, 24% PEGylated species (RP-HPLC), distribution of minor peaks, 12% FLP (IEX).

EXAMPLE 32

Purification of Crude NOX-G12-40 kDaYPEG (8) by Precipitation

Two 24 mL aliquots of the material generated in Example 21 were transferred into two 750 mL centrifuge bottles (Thermo Scientific Heraeus, Hanau, D), and 240 mL MeOH were added to each. The mixtures were thoroughly mixed, and stored at −20° for 2 hrs. The resulting precipitate was spun down (4000 g), the supernatant was decanted. The combined organic phase was concentrated to dryness. Recovery precipitate: 5300 OD, 90% PEGylated species (RP-HPLC), 57% FLP (IEX); Recovery supernatant: 4000 OD, 9% PEGylated species (RP-HPLC), distribution of minor peaks (IEX).

EXAMPLE 33

Purification of Crude TBA-40 kDaYPEG (9) by Precipitation

The material generated in Example 22 (21 mL) was transferred into a 750 mL centrifuge bottle (Thermo Scientific Heraeus, Hanau, D), and 250 mL MeOH were added. The mixture was thoroughly mixed, and stored at −20° for 2 hrs. The resulting precipitate was spun down (4000 g), the supernatant was decanted. The combined organic phase was concentrated to dryness. Recovery precipitate: 4410 OD, 96% PEGylated species (RP-HPLC), 87% FLP (IEX); Recovery supernatant: 830 OD, 9% PEGylated species (RP-HPLC), distribution of minor peaks, 13% FLP (IEX).

EXAMPLE 34

Synthesis of NOX-E36-40 kDaYPEG (1) (Combined Process)

Applying the procedure described in Example 2, 11.3 g L-rG CPG (600 Å, 70 µmol/g, 793 µmol) were used to assemble 5'NH$_2$—NOX-E36 (1 prePEG) with 2 Eq. of amidite per nucleotide coupling cycle. Yield: 164000 OD, Purity: 53%, Mass: 12966, (calc.: 12996). Next, 164kOD 5'NH$_2$—NOX-E36 (6.55 g, 58% FLP, 267 µmol) were reacted with a total of 23.3 g (583 µmol) 40 kDaYPEG-NHS-Ester (JenKem Technology, Allen, Tex., USA) in the presence of 18.1 g (56.1 mmol) Bu$_4$NBr, 12.3 mL (70.6 mmol) DIPEA in 696 mL DMF/H2O (3.25/1, v/v) applying the procedure described in Example 12. Monitoring of the reaction by RP-HPLC showed 70% conversion. IEX analysis showed 43% FLP of PEGylated product. Two aliquots of 32 mL (15000 OD, 43% FLP) were transferred into two 750 mL centrifuge bottles (Thermo Scientific Heraeus, Hanau, D), and 320 mL MeOH were added to each. The solutions were thoroughly mixed, and stored at −20° for 2 hrs. The resulting precipitate was spun down (4000 g), the supernatant was decanted. The residue was dissolved in 150 mL H$_2$O. Recovery: 9237 OD, 68% FLP (IEX), 97% FLP×OD recovery. A 8900 OD sample of this solution was charged on a 89 mL SourceQ IEX column (100 OD/mL resin, 50° C., 20 mL/min) and eluted by applying a gradient of the following buffer system (buffer A: 25 mM Tris, pH 7.5, 10% ACN; buffer B: 25 mM Tris, 2M NaCl, pH 7.5, 10% ACN; gradient: 5% B to 25% B in 30 min, 30 mL/min). During the loading a break-through of 1450 OD (68% FLP, 16% FLP×OD recovery) was detected. All product containing fractions (FLP≥80% FLP) were combined (6080 OD) and desalted by UF using a 5 K regenerated cellulose membrane (Millipore, Bedford, Mass.) and finally freeze dried. Yield: 5013 OD, 83% FLP, 69% FLP×OD recovery).

EXAMPLE 35

PEGylation Reaction

The amino-modified (deoxy-)oligonucleotide to be reacted was dissolved in water (1000 OD/mL). DMSO (2 mL), DIPEA (75 µL/mL oligonucleotide solution) and PEG-NHS (JenKem Technology, Allen, Tex., USA) dissolved in ACN (1.5 Eq with respect to full length product in ACN, 4.5 mL/g) was added successively to the oligonucleotide solution. The reaction mixture was agitated vigorously for 30 min and the reaction followed by RP-HPLC. If necessary, additional PEG-NHS dissolved in ACN was added to drive the reaction to completion. After complete conversion the reaction was stopped by addition of AcOH (80%, 37.5 µL/mL oligonucleotide solution).

EXAMPLE 36

Synthesis of NOX-E36-40 kDaPEG (1)

Applying the procedure described in Example 35, 6000 OD (240 mg, 54% FLP, 9.23 µmol) 5'NH$_2$—NOX-E36 (1 prePEG) were reacted with a total of 738 mg (18.5 µmol) 40 kDaYPEG-NHS dissolved 3.5 mL ACN in the presence of 466 µL (2.66 mmol) DIPEA in 18 mL DMSO/H$_2$O (2/1, v/v). Monitoring of the reaction by RP-HPLC showed 63% conversion.

EXAMPLE 37

Purification of Crude NOX-E36-40 kDaYPEG (1) by Precipitation

A 1000 OD (3.5 mL) sample of the material generated in Example 36 was transferred to a falcon tube, 10.5 mL MeOH were added. The mixture was thoroughly vortexed, and stored at −20° for 30 min. The resulting precipitate was spun down (4000 g), the supernatant was decanted. The combined organic phase was concentrated to dryness. Recovery precipitate: 695 OD, 95% PEGylated species (RP-HPLC), 65% FLP (IEX); Recovery supernatant: 277 OD, 0% PEGylated species (RP-HPLC), distribution of minor peaks (IEX).

EXAMPLE 38

Purification of Crude NOX-E36-40 kDaYPEG (1) by Precipitation

A 1000 OD (3.5 mL) sample of the material generated in Example 36 was transferred to a falcon tube and stored at 4° for 16 h. The resulting precipitate was spun down (4000 g), the supernatant was decanted. The combined organic phase was concentrated to dryness. Recovery precipitate: 618 OD, 86% PEGylated species (RP-HPLC), 65% FLP (IEX); Recovery supernatant: 330 OD, 0% PEGylated species (RP-HPLC), distribution of minor peaks (IEX).

EXAMPLE 39

Purification of Crude NOX-E36-40 kDaYPEG (1) by Precipitation

A 1000 OD (3.5 mL) sample of the material generated in Example 36 was transferred to a falcon tube and stored at 4° for 16 h. To the precipitate 17 mL DMSO/H$_2$O (2/1, v/v, 4° C.) was added and thoroughly mixed. The resulting mixture was centrifuged (4000 g), the supernatant was decanted. The combined organic phase was concentrated to dryness. Recovery precipitate: 540 OD, 95% PEGylated species (RP-HPLC), 66% FLP (IEX); Recovery supernatant: 371 OD, 1% PEGylated species (RP-HPLC), distribution of minor peaks (IEX).

EXAMPLE 40

Purification of Crude NOX-E36-40 kDaYPEG (1) by Precipitation

A 1000 OD (3.5 mL) sample of the material generated in Example 36 was transferred to a falcon tube and stored at −20° for 16 h. The resulting precipitate was spun down (4000 g), the supernatant was decanted. The combined organic phase was concentrated to dryness. Recovery precipitate: 601 OD, 86% PEGylated species (RP-HPLC), 50% FLP (IEX); Recovery supernatant: 341 OD, 2% PEGylated species (RP-HPLC), distribution of minor peaks (IEX).

The features of the present invention disclosed in the specification, the claims and/or the drawings may both separately and in any combination thereof be material for realizing the invention in various forms thereof.

---

I claim:

1. A method for obtaining a polyalkoxylated nucleic acid molecule comprising separating said polyalkoxylated nucleic acid molecule from a liquid mixture comprising said polyalkoxylated nucleic acid molecule and a non-polyalkoxylated nucleic acid molecule by precipitating said polyalkoxylated nucleic acid molecule from said mixture,
   wherein said mixture comprises a solution comprising a solvent or a mixture of solvents;
   wherein said polyalkoxylated nucleic acid molecule comprises a nucleic acid moiety and a polyalkoxylate moiety, and said non-polyalkoxylated nucleic acid molecule comprises a nucleic acid moiety and is lacking a polyalkoxylate moiety;
   wherein said polyalkoxylated nucleic acid molecule comprises a plurality of polyalkoxylated nucleic acid molecules comprising a plurality of nucleic acid moieties;

wherein said non-polyalkoxylated nucleic acid molecule comprises a plurality of non-polyalkoxylated nucleic acid molecules comprising a plurality of nucleic acid moieties; and wherein said precipitated polyalkoxylated nucleic acid molecule is separated from said non-polyalkoxylated nucleic acid molecule by separating liquid from solid.

2. The method according to claim 1, wherein said solvent comprises water and/or a water miscible organic solvent.

3. The method according to claim 1, wherein said precipitating comprises a temperature of 50° C. to 30° C.; a temperature of −25° C. to 25° C.; a temperature of −20° C. to 4° C.; a temperature of −20° C.; or a temperature of 4° C.

4. The method according to claim 1, wherein said precipitating comprises a pH range of 4 to 11; a pH range of 6 to 10; or a pH range of 7 to 9.5.

5. The method according to claim 1, wherein said precipitating is carried out until 75% to 100% of said polyalkoxylated nucleic acid molecule is precipitated; or until 90% to 100% of said polyalkoxylated nucleic acid molecule is precipitated.

6. The method according to claim 1, wherein said polyalkoxylate moiety comprises polyethylene glycol, polypropylene glycol, polybutylene glycol or polyglycerol.

7. The method according to claim 1, wherein said polyalkoxylate moiety comprises a molecular weight of 5,000 Da to 100,000 Da.

8. A method for preparing a polyalkoxylated nucleic acid molecule comprising a nucleic acid moiety and a polyalkoxylate moiety, comprising reacting a nucleic acid molecule with a polyalkoxylate in presence of a quaternary ammonium compound forming said polyalkoxylated nucleic acid molecule, wherein said nucleic acid molecule forms said nucleic acid moiety of said polyalkoxylated nucleic acid molecule; said polyalkoxylate forms said polyalkoxylate moiety of said polyalkoxylated nucleic acid molecule; and said quaternary ammonium compound is dissolved in water, in a water miscible organic solvent, or in a combination thereof, wherein said nucleic acid molecule comprises a reactive group, wherein when there is more than one reactive group, said reactive groups are different, and said polyalkoxylate comprises a reactive group that reacts with said nucleic acid molecule comprising a reactive group of the nucleic acid molecule forming said polyalkoxylated nucleic acid molecule;

wherein said reactive group of said nucleic acid molecule comprises an amine, a thiol, an azide, an alkyne, a carboxylate, a carboxylic acid ester, an aldehyde, an iodoalkyl or a maleimide; and wherein said reactive group of the polyalkoxylate comprises an amine, a thiol, an azide, an alkyne, a carboxylate, a carboxylic acid ester, an aldehyde, an N-hydroxysuccinimide, an iodoalkyl or a maleimide.

9. The method according to claim 8, wherein said quaternary ammonium compound comprises tetraalkylammonium chloride, tetraalkylammonium bromide, tetraalkylammonium tetrafluoroborate tetraalkylammonium hexafluorophosphate, tetraalkylammonium hydrogen sulphate or tetraalkylammonium dihydrogen phosphate, wherein alkyl is an alkyl chain of 1 to 18 C atoms.

10. The method according to claim 8, wherein said water miscible organic solvent comprises dimethyl sulfoxide, diethyl sulfoxide, methyl ethyl sulfoxide, methyl formamide, dimethyl formamide, ethyl formamide, ethyl methyl formamide, diethyl formamide, 2-pyrrolidone, N-methyl-2-pyrrolidone, N-ethyl-2-pyrrolidone, acetonitrile, acetone, ethyl methyl ketone, methyl propyl ketone, diethyl ketone, methyl isopropyl ketone, methyl formate, ethyl formate, propyl formate, isopropyl formate, methyl acetate, ethyl acetate, methyl propanoate, tetrahydrofuran or dioxan.

11. The method according to claim 8, wherein said reacting comprises 1 to 20 mole or 2 to 10 mole equivalents of said quaternary ammonium compound per nucleotide of said nucleic acid molecule.

12. The method according to claim 8, wherein said reacting comprises a temperature of 10° C. to 50° C. or a temperature of 20° C. to 40° C.

13. The method according to claim 8, wherein said reacting comprises a pH range of 4 to 11 or a pH range of 6 to 10.

14. The method according to claim 8, wherein said polyalkoxylate moiety comprises a molecular weight of 5,000 Da to 100,000 Da.

15. The method according to claim 8, wherein said polyalkoxylate moiety comprises polyethylene glycol, polypropylene glycol, polybutylene glycol or polyglycerol.

16. The method according to claim 8, wherein said quaternary ammonium compound comprises tetrabutylammonium bromide.

17. The method according to claim 8, wherein said reactive group of said nucleic acid molecule comprises an amine and said reactive group of said polyalkoxylate comprises a carboxylic acid ester.

* * * * *